(12) United States Patent
Roberts et al.

(10) Patent No.: US 9,470,681 B2
(45) Date of Patent: Oct. 18, 2016

(54) APPARATUSES FOR DETERMINING WHETHER A SUBSTANCE IS CARRIED IN A FLUID

(75) Inventors: Deborah Roberts, Kelowna (CA); Mina Hoorfar, Kelowna (CA); Sina Jomeh, Kelowna (CA); Rony Das, Kelowna (CA)

(73) Assignee: The University of British Columbia, Vancouver (CA)

( * ) Notice: Subject to any disclaimer, the term of this patent is extended or adjusted under 35 U.S.C. 154(b) by 458 days.

(21) Appl. No.: 13/522,230

(22) PCT Filed: Jan. 14, 2011

(86) PCT No.: PCT/CA2011/000051
§ 371 (c)(1),
(2), (4) Date: Jul. 13, 2012

(87) PCT Pub. No.: WO2011/085490
PCT Pub. Date: Jul. 21, 2011

(65) Prior Publication Data
US 2013/0045893 A1    Feb. 21, 2013

Related U.S. Application Data

(60) Provisional application No. 61/295,097, filed on Jan. 14, 2010.

(51) Int. Cl.
*C12M 1/34*    (2006.01)
*G01N 33/543*    (2006.01)

(52) U.S. Cl.
CPC .. *G01N 33/54306* (2013.01); *G01N 33/54366* (2013.01)

(58) Field of Classification Search
USPC ....... 422/400, 401, 402, 405, 408, 425, 430; 435/287.2, 287.9; 436/810
See application file for complete search history.

(56) References Cited

U.S. PATENT DOCUMENTS

| | | | | |
|---|---|---|---|---|
| 3,001,914 A | * | 9/1961 | Andersen | ........................ 435/30 |
| 3,795,135 A | | 3/1974 | Andersen | |
| 4,116,638 A | * | 9/1978 | Kenoff | .................... B01L 3/502 |
| | | | | 15/304 |
| 4,197,287 A | * | 4/1980 | Piasio | .................... G01N 33/50 |
| | | | | 422/562 |

(Continued)

FOREIGN PATENT DOCUMENTS

WO    WO 2005/001411 A2    1/2005
WO    WO 2009/077913 A1    6/2009

OTHER PUBLICATIONS

Bensinger, Floyd A. Spring 2009 Today's Boiler pp. 10-12 and 14.*

(Continued)

*Primary Examiner* — Chris L Chin
(74) *Attorney, Agent, or Firm* — Klarquist Sparkman, LLP

(57) ABSTRACT

Apparatuses for determining whether a substance is carried in a fluid are disclosed. One such apparatus includes a body having: a plurality of spaced-apart capture surfaces configured to contact the fluid and capture the substance from the fluid; and a plurality of fluid guiding surfaces spaced apart by a predetermined distance from respective at least portions of respective ones of the plurality of capture surfaces. Another such apparatus includes: a fluid conduit to direct flow of the fluid; and at least one element removably positioned in the fluid conduit and having at least one capture surface configured to contact the fluid and capture the substance from the fluid.

19 Claims, 24 Drawing Sheets

(56) References Cited

U.S. PATENT DOCUMENTS

| | | | |
|---|---|---|---|
| 4,225,575 A * | 9/1980 | Piasio | C12Q 1/00 422/417 |
| 7,727,775 B2 | 6/2010 | Willson et al. | |
| 2004/0022700 A1* | 2/2004 | Kim et al. | 422/186.3 |
| 2004/0029261 A1* | 2/2004 | Oldfield | 435/287.2 |
| 2006/0088946 A1 | 4/2006 | Willson et al. | |
| 2006/0195040 A1* | 8/2006 | Nason et al. | 600/532 |
| 2006/0246501 A1 | 11/2006 | Northrup | |
| 2008/0185295 A1* | 8/2008 | Briman et al. | 205/777.5 |
| 2010/0003666 A1 | 1/2010 | Lee et al. | |

OTHER PUBLICATIONS

Disney et al 2004 JACS 126: 13343-13346.*

Cozens-Roberts et al., "Receptor-mediated cell attachment and detachment kinetics. II. Experimental model studies with the radial-flow detachment assay," *Biophysical Journal*, 1990, 58(4):857-872, Biophysical Society, Rockville, Maryland.

Das et al., "A rapid, robust, ultra-sensitive, and close to real-time assay for capture and detection of waterborne pathogens," American Water Work Association's Annual Conference and Exhibition ACE 10, Jun. 22, 2010, Chicago, Illinois.

Das et al., "Antibody Immobilization and its Application to *Cryptosporidium* Detection (Poster)," BC Water Symposium, Aug. 30, 2010, Kelowna, British Columbia, Canada.

Das et al., "Development of a near real-time device for the detection of *Cryptosporidium* in water," 11th Pacific Canadian Symposium on Water Quality Research, May 4, 2010, Whistler, British Columbia, Canada.

Das et al., "Antibody Immobilization and its Application to *Cryptosporidium* detection (Poster)," BCWWA 2011 Annual Conference, Apr. 16, 2011, Kelowna, British Columbia, Canada.

Das, "Development of a near real-time device for the detection of *Cryptosporidium* in water," Graduate Seminar Series, School of Engineering, University of British Columbia, Apr. 29, 2010, Kelowna, British Columbia, Canada.

Jomeh et al., "Numerical Investigation of the Effect of Geometric and Physiochemical Parameters on Biomolecule Capture Efficiency," *Proceedings of ASME 2010 3rd Joint US-European Fluids Engineering Summer Meeting and 8th International Conference on Nanochannels, Microchannels, and Minichannels, FEDSM2010-ICNMM2010*, Aug. 1-5, 2010, Montreal, Canada, pp. 1253-1260.

Jomeh et al., "Numerical Modeling of Mass Transport in Microfluidic Biomolecule-Capturing Devices Equipped with Reactive Surfaces," *Chemical Engineering Journal*, Dec. 1, 2010, pp. 668-677, vol. 165, No. 2, Elsevier B.V.

Jomeh et al., "Development of a capture device for rapid detection of waterborne pathogens, Research Seminar," School of Engineering, University of British Columbia, 2011.

Jomeh et al., "Study of the effect of electrophoresis on transport of biomolecules in microreactors," *Proceedings of the ASME 2011 9th International Conference on Nanochannels, Microchannels, and Minichannels (ICNMM2011)*, Jun. 19-22, 2011, Edmonton, Alberta, Canada.

Jomeh et al., "Study of the effect of electric field and electroneutrality on transport of biomolecules in microreactors," *Microfluid Nanfluid*, received May 30, 2011, accepted Aug. 10, 2011, published online Aug. 26, 2011, pp. 279-294, issue 12, Springer-Verlag.

Jomeh et al., "Numerical simulation of the adhesion of a moving biological cell on a reactive substrate in a rectangular microchannel," *ASME 2012 10th International Conference on Nanochannels, Microchannels, and Minichannels (ICNMM2012)*, Jun. 8-12, 2012, Puerto Rico.

Jomeh et al., "Development of a rapid capture flow cell for detection of harmful microorganisms in drinking water," BC Water and Waste Association Annual Conference, Apr. 20-23, 2012, Penticton, British Columbia, Canada.

Jomeh et al., "Development of a capture device for rapid detection of waterborne pathogens," Research Seminar, School of Engineering, University of British Columbia, 2012.

Jomeh, "Development of a microfluidic capture device for the manipulation and concentration of waterborne pathogens with the focus on *Cryptosporidium parvum* oocysts," Ph. D. Thesis, Feb. 2013, University of British Columbia Okanagan.

Jomeh, et al., "Microfluidic separation and concentration of Cryptosporidium oocysts in finished water," submitted to *Water Research*, Jul. 2013.

Oleschuk et al., "Trapping of Bead-Based Reagents within Microfluidic Systems: On-Chip Solid-Phase Extraction and Electrochromatography, *Analytical Chemistry*," published on Web Dec. 28, 1999, pp. 585-590, vol. 72, No. 3, American Chemical Society.

Roberts et al., "Development of a near real-time device for the detection of pathogens in water," Presented to the Center for Integrated Bio and Nano Systems, Dec. 2, 2010, University of Houston.

Roberts et al., "What's on your mind? Is What's in Your Water on Your Mind: Development of a near real-time device for the detection of pathogens in water," Mar. 8, 2010, University of British Columbia Okanagan.

\* cited by examiner

APPARATUSES FOR DETERMINING WHETHER A SUBSTANCE IS CARRIED IN A FLUID

RELATED APPLICATION

This is the U.S. National Stage of International Application No. PCT/CA2011/000051, filed Jan. 14, 2011, which was published in English under PCT Article 21(2), which in turn claims the benefit of U.S. Provisional Patent Application No. 61/295,097 entitled ROBUST METHOD FOR CAPTURE AND DETECTION OF WATERBORNE PATHOGENS and filed on Jan. 14, 2010, which is incorporated herein by reference.

BACKGROUND

1. Field

The invention relates generally to apparatuses for determining whether a substance is carried in a fluid.

2. Related Art

In some circumstances, it may be desirable to determine whether a substance is carried in a fluid. For example, various pathogens may be present in water intended for human consumption, and determining whether such pathogens are present in such water may advantageously prevent consumption of such pathogens and thus prevent waterborne disease.

One method for determining whether pathogens are present in water involves measuring turbidity of the water. However, turbidity may indicate substances other than pathogens, and also pathogens may be present in relatively clear water. Therefore, measuring turbidity of water may be an unreliable method for determining whether pathogens are present in the water.

Another method for determining whether pathogens are present in water involves measuring a quantity of coliform bacteria in the water. Coliform bacteria are naturally present in the digestive tracts of many animals, and therefore may indicate fecal contamination in the water. However, coliform bacteria in the water may not reveal some other pathogens in the water, and measuring a quantity of coliform bacteria may require 24 to 48 hours, for example, for growth of the coliform bacteria to a measurable quantity.

Another method for determining whether protozoan pathogens (such as *Cryptosporidium parvum* or *Giardia lamblia*, for example) are present in water involves filtering the water and examining the filter for such pathogens. However, filtering water may not reveal smaller pathogens, and examining a filter for protozoan pathogens may require time-consuming laboratory analysis.

Another method for determining whether pathogens are present in water involves passing the water over a plurality of beads having capture surfaces configured to capture the pathogens. An apparatus including such a plurality of beads may be referred to as a "packed bed" apparatus. However, in such an apparatus, the spaces between the surfaces of the beads are inconsistent. In some regions, the space between adjacent beads may be so small that water flow on such regions is unduly restricted. In other regions, the space between adjacent beads may be so large that some pathogens in the water pass between the adjacent beads sufficiently far from the capture surfaces that the pathogens escape capture. Such inconsistent spacing may therefore decrease efficiency of such a packed bed apparatus.

SUMMARY

In accordance with one illustrative embodiment, there is provided an apparatus for determining whether a substance is carried in a fluid. The apparatus includes a body having: a plurality of spaced-apart capture surfaces configured to contact the fluid and capture the substance from the fluid; and a plurality of fluid guiding surfaces spaced apart by a predetermined distance from respective at least portions of respective ones of the plurality of capture surfaces.

The body may define a fluid conduit surrounding the plurality of capture surfaces to direct flow of the fluid.

The capture surfaces may be coated with a plurality of capture molecules having respective binding affinities with the substance.

The capture molecules may include proteins. The proteins may include antibodies, antibody fragments, lectins, or protein aptamers.

The capture molecules may include nucleic acids. The nucleic acids may include nucleic acid aptamers.

The body may include at least one element having the capture surfaces. The at least one element may be removable.

The at least one element may include a plurality of cylindrical elements.

The plurality of fluid guiding surfaces may include, for each one of the plurality of capture surfaces, at least a portion of a surface of an adjacent one of the plurality of cylindrical elements.

The cylindrical elements may extend generally parallel to each other.

The at least one element may include a plurality of longitudinally spaced-apart plates each having at least one of the plurality of capture surfaces.

Each one of the plurality of plates may define at least one longitudinal fluid through-opening longitudinally aligned with the at least one wall of each adjacent one of the plurality of plates.

The plurality of fluid guiding surfaces may include, for each one of the plurality of capture surfaces, at least a portion of a surface of the at least one wall of an adjacent one of the plurality of plates.

The apparatus may further include at least one spacer separating adjacent ones of the plurality of plates.

The at least one spacer may surround a respective region between adjacent ones of the plurality of plates and in fluid communication with the at least one fluid through-opening of the adjacent ones of the plurality of plates.

Each spacer may have a thickness equal to the predetermined distance.

The at least one spacer may seal the respective region.

The apparatus may further include a plurality of longitudinally spaced walls longitudinally spaced from opposite sides of each one of the plurality of plates and defining a respective region surrounding each one of the plurality of plates.

The body may define at least one opening for communicating fluid between adjacent ones of the regions. The plurality of fluid guiding surfaces may include, for each one of the plurality of capture surfaces, at least a portion of a surface an adjacent one of the plurality of walls.

Each one of the plurality of plates may have first and second opposite and generally circular sides each having a center and a peripheral region. The at least one opening may be configured to communicate fluid between the centers of adjacent sides of adjacent ones of the plurality of plates. For each one of the plurality of plates, the respective region surrounding the plate may be configured to direct fluid received at the center of the first side of the plate to the peripheral region of the first side of the plate, then to the peripheral region of the second side of the plate, and then to the center of the second side of the plate.

The plates may extend generally parallel to each other.

The plurality of capture surfaces and the plurality of fluid guiding surfaces may be configured to generate electric fields between each one of the plurality of capture surfaces and each respective one of the plurality of fluid guiding surfaces.

Each one of the plurality of spaced-apart capture surfaces may be electrically grounded, and each one of the plurality of fluid guiding surfaces may be electrically connected to a voltage source.

At least one of the plurality of capture surfaces may be oriented in the apparatus to be contacted by the fluid in an incidental flow.

In accordance with another illustrative embodiment, there is provided an apparatus for determining whether a substance is carried in a fluid. The apparatus includes: a fluid conduit to direct flow of the fluid; and at least one element removably positioned in the fluid conduit and having at least one capture surface configured to contact the fluid and capture the substance from the fluid.

The at least one capture surface may be coated with a plurality of capture molecules having respective binding affinities with the substance.

The capture molecules may include proteins. The proteins may include antibodies, antibody fragments, lectins, or protein aptamers.

The capture molecules may include nucleic acids. The nucleic acids may include nucleic acid aptamers.

The apparatus may further include a plurality of fluid guiding surfaces spaced apart by a predetermined distance from respective at least portions of respective ones of the plurality of capture surfaces.

The at least one element may include a plurality of cylindrical elements.

The plurality of fluid guiding surfaces may include, for each one of the plurality of capture surfaces, at least a portion of a surface of an adjacent one of the plurality of cylindrical elements.

The cylindrical elements may extend generally parallel to each other.

The at least one element may include a plurality of longitudinally spaced-apart plates each having at least one of the plurality of capture surfaces.

Each one of the plurality of plates may have at least one wall and may defines at least one longitudinal fluid through-opening longitudinally aligned with the at least one wall of each adjacent one of the plurality of plates.

The plurality of fluid guiding surfaces may include, for each one of the plurality of capture surfaces, at least a portion of a surface of the at least one wall of an adjacent one of the plurality of plates.

The apparatus may further include at least one spacer separating adjacent ones of the plurality of plates.

The at least one spacer may surround a respective region between adjacent ones of the plurality of plates and in fluid communication with the at least one fluid through-opening of the adjacent ones of the plurality of plates.

Each spacer may have a thickness equal to the predetermined distance.

The at least one spacer may seal the respective region.

The apparatus may further include a plurality of longitudinally spaced walls longitudinally spaced from opposite sides of each one of the plurality of plates and defining a respective region surrounding each one of the plurality of plates. The apparatus may define at least one opening for communicating fluid between adjacent ones of the regions. The plurality of fluid guiding surfaces may include, for each one of the plurality of capture surfaces, at least a portion of a surface an adjacent one of the plurality of walls.

Each one of the plurality of plates may have first and second opposite and generally circular sides each having a center and a peripheral region. The at least one opening may be configured to communicate fluid between the centers of adjacent sides of adjacent ones of the plurality of plates. For each one of the plurality of plates, the respective region surrounding the plate may be configured to direct fluid received at the center of the first side of the plate to the peripheral region of the first side of the plate, then to the peripheral region of the second side of the plate, and then to the center of the second side of the plate.

The plurality of capture surfaces and the plurality of fluid guiding surfaces may be configured to generate electric fields between each one of the plurality of capture surfaces and each respective one of the plurality of fluid guiding surfaces.

Each one of the plurality of spaced-apart capture surfaces may be electrically grounded, and each one of the plurality of fluid guiding surfaces may be electrically connected to a voltage source.

At least one of the plurality of capture surfaces may be oriented in the apparatus to be contacted by the fluid in an incidental flow.

Other aspects and features of the present invention will become apparent to those ordinarily skilled in the art upon review of the following description of specific embodiments in conjunction with the accompanying figures.

BRIEF DESCRIPTION OF THE DRAWINGS

In drawings that illustrate various embodiments.

DETAILED DESCRIPTION

First Embodiment

Figure 1:
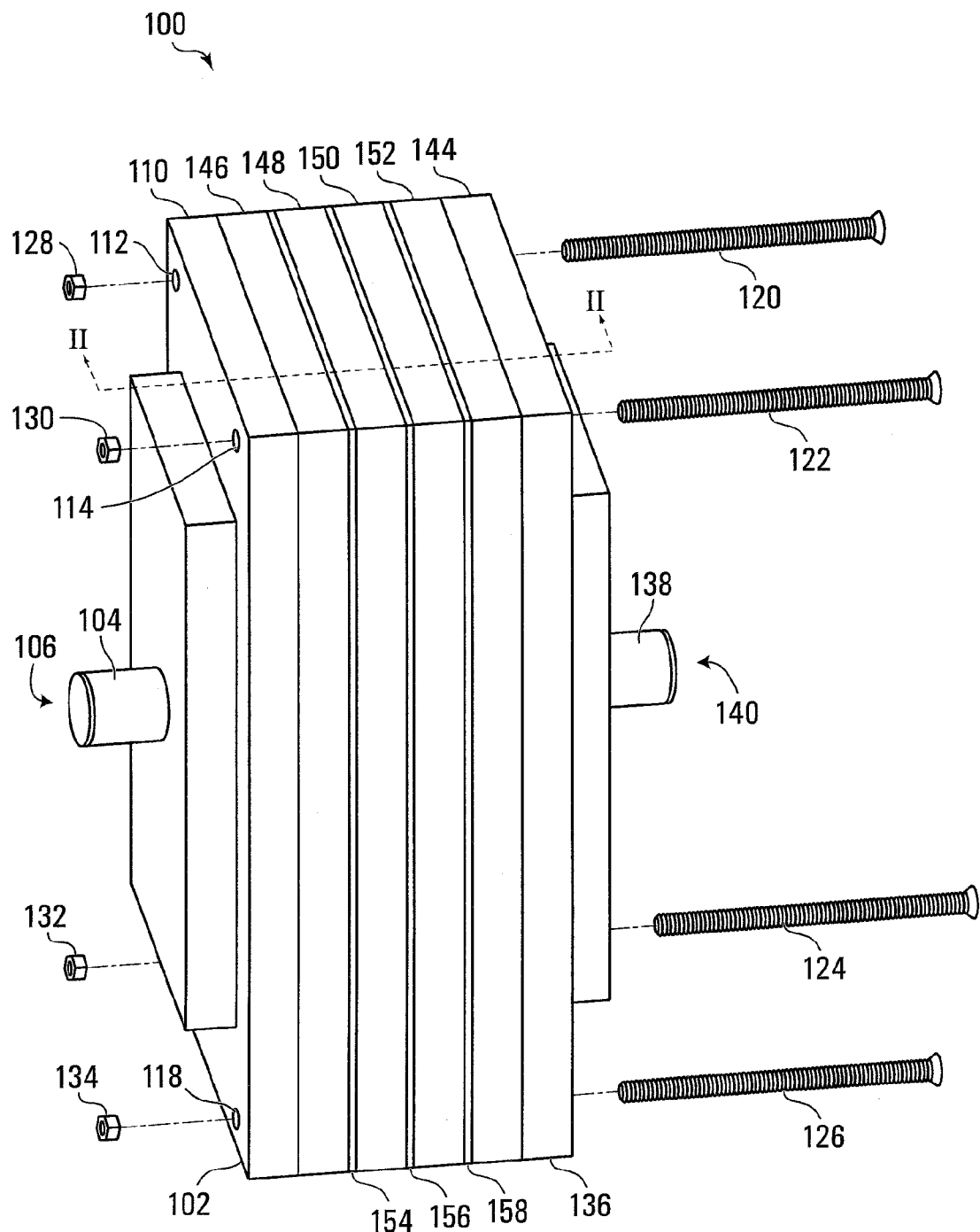
FIG. 1 is an oblique view of an illustrative apparatus for determining whether a substance is carried in a fluid.
Figure 2:
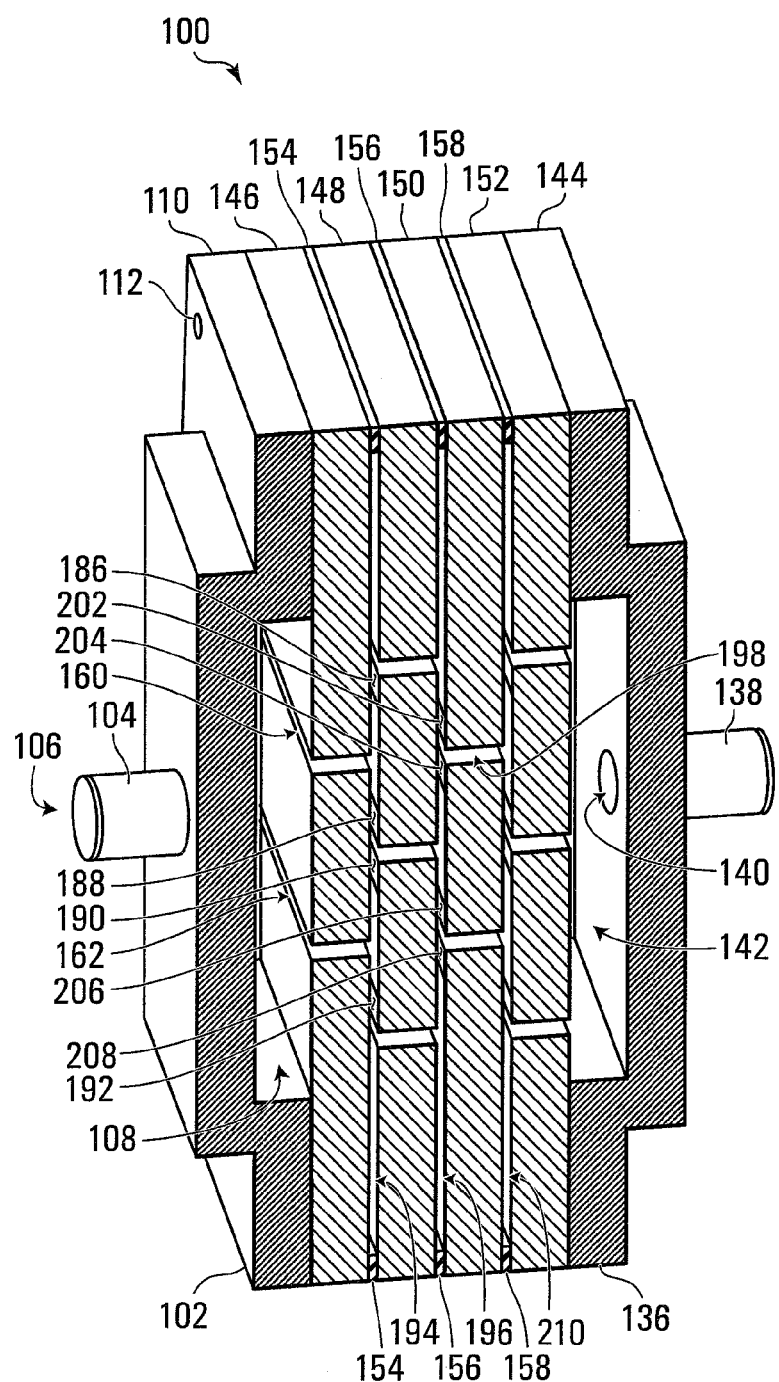
FIG. 2 is a cross-sectional view of the apparatus of FIG. 1 taken along the line II-II in FIG. 1.

Referring to FIGS. 1 and 2, an illustrative apparatus for determining whether a substance is carried in a fluid is shown generally at 100 and includes an inlet coupling unit 102. The inlet coupling unit 102 includes an inlet pipe portion 104 defining therethrough a fluid inlet shown generally at 106. The inlet coupling unit 102 defines a cavity shown generally at 108 and in fluid communication with the fluid inlet 106, and the inlet coupling unit 102 includes a flange 110 surrounding the cavity 108. The flange 110 defines four fastener through-openings (such as those shown generally at 112, 114, and 118) for receiving respective fasteners 120, 122, 124, and 126. In the embodiment shown, the fasteners 120, 122, 124, and 126 are threaded for threadedly engaging respective nuts 128, 130, 132, and 134.

The apparatus 100 also includes an outlet coupling unit 136 that includes an outlet pipe portion 138 defining therethrough a fluid outlet shown generally at 140. The outlet coupling unit 136 defines a cavity shown generally at 142 and in fluid communication with the fluid outlet 140, and the outlet coupling unit 136 includes a flange 144 surrounding the cavity 142. The flange 144 also defines fastener through-openings (not shown) for receiving the fasteners 120, 122, 124, and 126.

The apparatus 100 includes first, second, third, and fourth longitudinally spaced-apart plates 146, 148, 150, and 152, which may also be referred to as "elements". The apparatus 100 also includes a first separator 154 between the first and second plates 146 and 148, a second separator 156 between the second and third plates 148 and 150, and a third separator 158 between the third and fourth plates 150 and 152.

Figure 3:
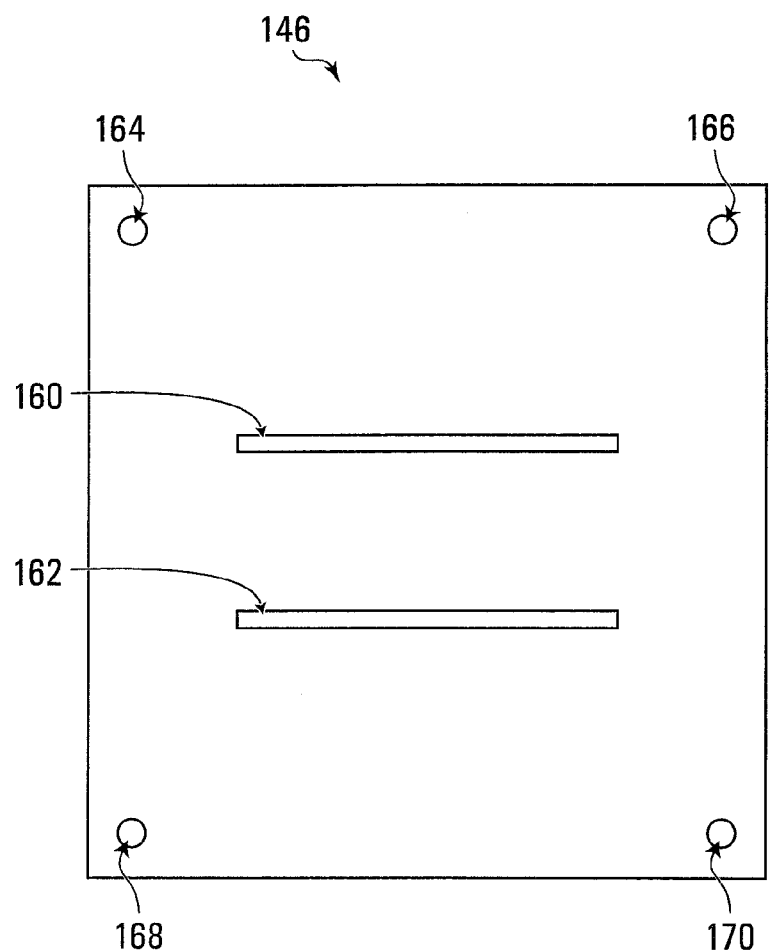
FIG. 3 is an elevational view of a first plate of the apparatus of FIG. 1.

Referring to FIG. 3, the first plate 146 defines elongate rectangular fluid through-openings shown generally at 160 and 162. Referring back to FIG. 2, the fluid through-openings 160 and 162 are positioned on the first plate 146 so that when the first plate 146 is positioned adjacent the flange 110, the fluid through-openings 160 and 162 are in fluid communication with the cavity 108. In general, the position, length, and width of the fluid through-openings 160 and 162 are determined based on the critical shear path of the flow, which is a function of the fluid viscosity and velocity and the physical properties of the substance, for example. Referring back to FIG. 3, the first plate 146 also defines fastener through-openings shown generally at 164, 166, 168, and 170 for receiving the fasteners 120, 122, 124, and 126 respectively. The portions of the first plate 146 other than the through-openings may be referred to as a "wall".

Figure 4:
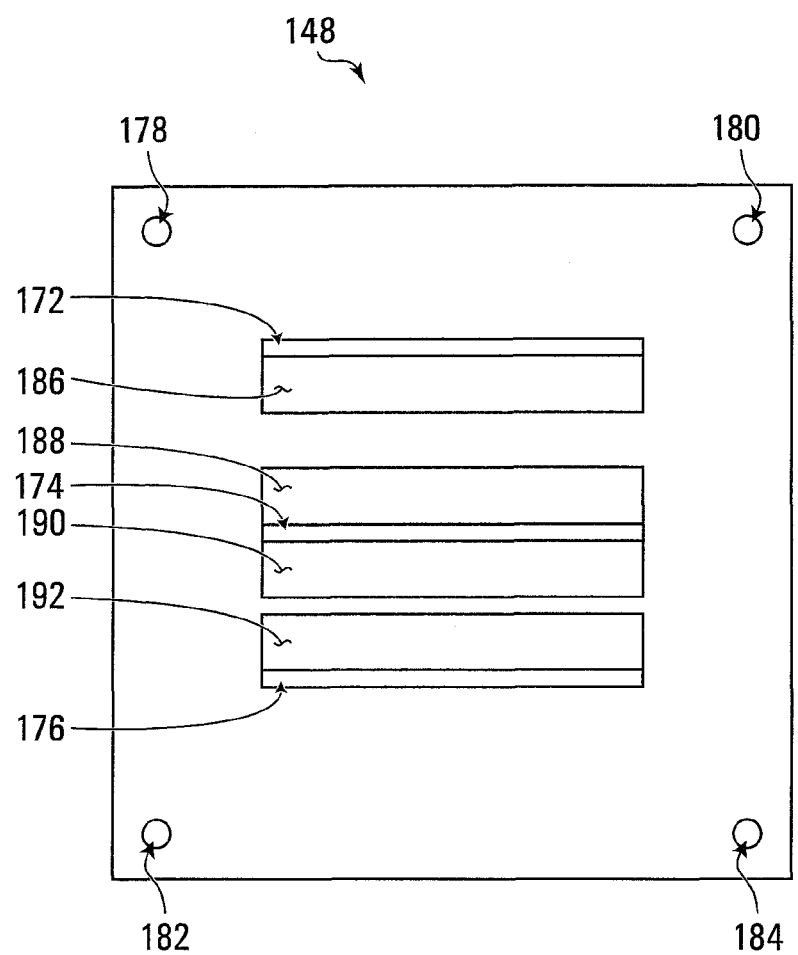
FIG. 4 is an elevational view of a second plate of the apparatus of FIG. 1.

Referring to FIG. 4, the second plate 148 defines elongate rectangular longitudinal fluid through-openings shown generally at 172, 174, and 176. The second plate 148 also defines fastener through-openings shown generally at 178, 180, 182, and 184 for receiving the fasteners 120, 122, 124, and 126 respectively. The portions of the second plate 148 other than the through-openings may be referred to as a "wall". The second plate 148 also has a first capture surface 186 proximate the fluid through-opening 172, second and third capture surfaces 188 and 190 proximate the fluid through-opening 174, and a fourth capture surface 192 proximate the fluid through-opening 176. The fourth plate 152 is substantially the same as the second plate 148.

The capture surfaces 186, 188, 190, and 192 are configured to capture one or more substances carried by a fluid proximate the capture surfaces. The substance may, for example, be a protozoan pathogen such as *Cryptosporidium parvum* or *Giardia lamblia*, a bacterial pathogen such as coliform, a virus, or a chemical contaminant. To capture such a substance, the capture surfaces 186, 188, 190, and 192 may be coated with a plurality of capture molecules (which may also be referred to as "ligands") having respective binding affinities with the substance. Capture molecules having such binding affinities may be identified by one skilled in the art depending on the substance to be captured. In general, such capture molecules may include, for example, proteins such as antibodies, antibody fragments, lectins, or protein aptamers, or nucleic acids such as nucleic acid aptamers. For example, the antibodies may include one or more of IgG, IgA, IgE, or IgM forms, and the antibody fragments may include one or more of Fab', F(ab')$_2$, and Fab forms. The capture molecules coated on the capture surfaces may have binding affinities for only one substance, such as a particular pathogen for example, or the capture molecules coated on the capture surfaces may include different capture molecules having respective binding affinities for respective different substances. Such different capture molecules may be arranged in arrays on the capture surfaces so that capture molecules having binding affinities for particular substances are in known positions on the capture surfaces. Such arrays advantageously permit identification of a detected substance based on the type of capture molecules known to be in the location where the substance is detected. The capture surfaces 186, 188, 190, and 192 may include one or more of silicon, glass (such as any type of silica or quartz, for example), plastic (such as polypropylene, poly(ethylene) terephthalate, polyethylene, poly(tetrafluroethylene), tetrafluroethylene, or polydimethylesiloxane, for example), metal (such as gold, for example), avidin, streptavidin, and protein A, or other hydrophobic materials known in the art of protein binding chemistry, for example, to facilitate adhesion of the capture molecules. For example, antibody fragments having a free —SH group may bond with gold to form a self-assemble monolayer.

Referring back to FIG. 2, when the first separator 154 is positioned adjacent the first plate 146 and the second plate 148 is positioned adjacent the first separator 154, the first and second plates 146 and 148 are separated by a first region shown generally at 194. The first region 194 is surrounded by the first separator 154 and has a thickness equal to a thickness of the first separator 154. The fluid through-openings 172, 174, and 176 are positioned on the second plate 148 so that when the first separator 154 is positioned adjacent the first plate 146 and the second plate 148 is positioned adjacent the first separator 154, the fluid through-openings 160, 162, 172, 174, and 176 are in fluid communication with the first region 194 and staggered relative to the fluid through-openings 160 and 162. When the first separator 154 is positioned adjacent the first plate 146 and the second plate 148 is positioned adjacent the first separator 154, the second plate 148 is longitudinally spaced apart from the first plate 146.

Fluid received in the first region 194 from the fluid through-opening 160 may be directed through one of the fluid through-openings 172 and 174; such fluid passes over one of the capture surfaces 186 and 188 so that the capture surfaces can capture a substance carried by the fluid. Also, fluid received in the first region 194 from the fluid through-opening 162 may be directed through one of the fluid through-openings 174 and 176; such fluid passes over one of the capture surfaces 190 and 192 so that the capture surfaces can capture a substance carried by the fluid.

Advantageously, when fluid passes from one of the fluid through-openings 160 and 162 to one of the fluid through-openings 172, 174, and 176, such fluid passes over one of the capture surfaces 186, 188, 190, and 192 within a predetermined distance of the capture surfaces, namely the thickness of the first region 194 as determined by the thickness of the first separator 154. Portions of the surface of the first plate 146 that are opposite the capture surfaces 186, 188, 190, and 192 are thus fluid guiding surfaces that are spaced apart from the capture surfaces 186, 188, 190, and 192 by that predetermined distance. The predetermined distance may be determined from properties such as electrophoresis mobility of the substance, flow rate of the fluid, and length of a flow path, for example. The fluid passes over the capture surfaces consistently at that predetermined distance, advantageously avoiding inefficiency from fluid passing over the capture surfaces at smaller or larger distances.

Still referring to FIG. 2, when the second separator 156 is positioned adjacent the second plate 148 and the third plate 150 is positioned adjacent the second separator 156, the second and third plates 148 and 150 are separated by a second region shown generally at 196. The second region 196 is surrounded by the second separator 156 and has a thickness equal to a thickness of the second separator 156.

Figure 5:
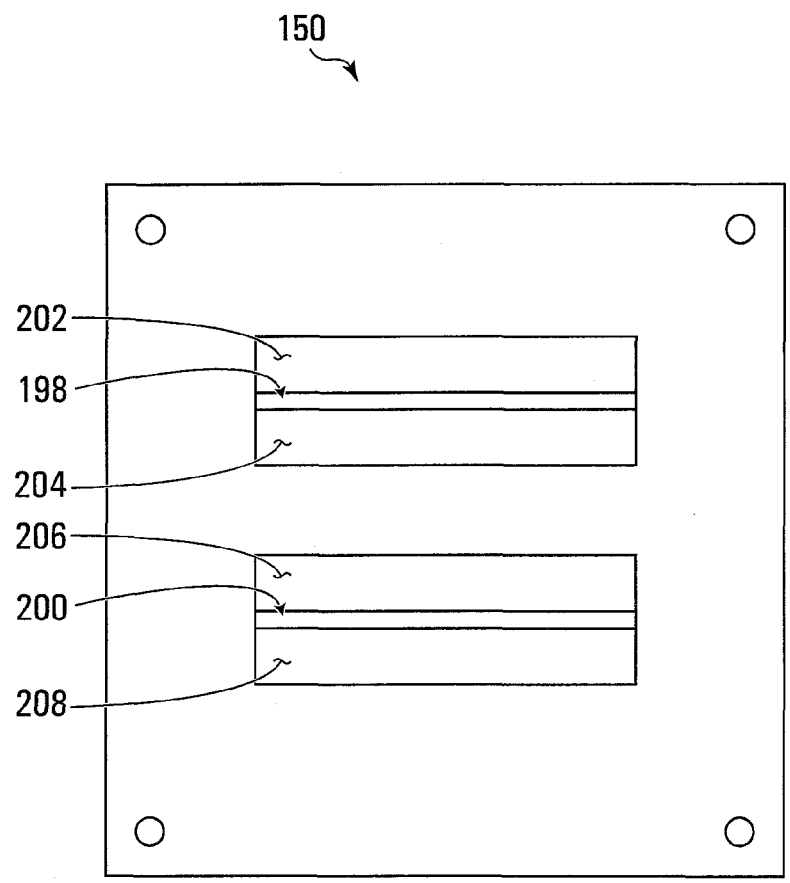
FIG. 5 is an elevational view of a third plate of the apparatus of FIG. 1.

Referring to FIG. 5, the third plate 150 is substantially the same as the first plate 146, and the third plate 150 defines elongate rectangular longitudinal fluid through-openings shown generally at 198 and 200 that are in substantially the same positions on the third plate 150 as the fluid through-openings 160 and 162 on the first plate 146. The portions of the third plate 150 other than the through-openings may be referred to as a "wall". However, the third plate also has first and second capture surfaces 202 and 204 proximate the fluid through-opening 198, and third and fourth capture surfaces 206 and 208 proximate the fluid through-opening 200. The capture surfaces 202, 204, 206, and 208 are coated with a plurality of capture molecules substantially as discussed above for the capture surfaces 186, 188, 190, and 192. When the second separator 156 is positioned adjacent the second plate 148 and the third plate 150 is positioned adjacent the second separator 156, the third plate 150 is longitudinally spaced apart from the second plate 148, and the capture surfaces 202, 204, 206, and 208 are thus spaced apart from the capture surfaces 186, 188, 190, and 192.

Referring back to FIG. 2, when the second separator 156 is positioned adjacent the second plate 148 and the third plate 150 is positioned adjacent the second separator 156, the fluid through-openings 172, 174, and 176 of the second plate 148 and the fluid through-openings 198 and 200 of the third plate 150 are in fluid communication with the second region 196. Further, fluid received in the second region 196 from the fluid through-opening 172 may be directed through the fluid through-opening 198; such fluid passes over the capture surface 202. Also, fluid received in the second region 196 from the fluid through-opening 174 may be directed through one of the fluid through-openings 198 and 200; such fluid passes over one of the capture surfaces 204 and 206. Also, fluid received in the second region 196 from the fluid through-opening 176 may be directed through the fluid through-opening 200; such fluid passes over the capture surface 208.

Advantageously, when fluid passes from one of the fluid through-openings 172, 174, and 176 to one of the fluid through-openings 198 and 200, such fluid passes over one of the capture surfaces 202, 204, 206, and 208 within a predetermined distance of the capture surfaces, namely the thickness of the second region 196 as determined by the thickness of the second separator 156. Portions of the surface of the second plate 148 that are opposite the capture surfaces 202, 204, 206, and 208 are thus fluid guiding surfaces that are spaced apart from the capture surfaces 202, 204, 206, and 208 by that predetermined distance. Again, fluid passes over the capture surfaces consistently at a predetermined distance, advantageously avoiding inefficiency from fluid passing over the capture surfaces at smaller or larger distances.

Still referring to FIG. 2, when the third separator 158 is positioned adjacent the third plate 150 and the fourth plate 152 is positioned adjacent the third separator 158, the third and fourth plates 150 and 152 are longitudinally spaced-apart and separated by a third region shown generally at 210. The third region 210 is surrounded by the third separator 158 and has a thickness equal to a thickness of the third separator 158. The fluid through-openings of the third and fourth plates 150 and 152 are in fluid communication with the third region 210, and the capture surfaces and fluid through-openings of the fourth plate 152 function substantially the same as the capture surfaces and fluid through-openings of the second plate 148 as described above.

Also, when the outlet coupling unit 136 is positioned adjacent the fourth plate 152, the fluid through-openings of the fourth plate 152 are in fluid communication with the cavity 142. Thus the coupling units 102 and 136, the plates 146, 148, 150, and 152, and the separators 154, 156, and 158 form a fluid conduit between the inlet 106 and the outlet 140. In the embodiment shown, the separators 154, 156, and 158 seal the regions 194, 196, and 210 respectively to prevent leakage from the fluid conduit, and the fasteners 120, 122, 124, and 126 may be tightened to facilitate such sealing and form a body including the coupling units 102 and 136, the plates 146, 148, 150, and 152, and the separators 154, 156, and 158. Further, the fasteners 120, 122, 124, and 126 may be removed from the apparatus to release the plates 146, 148, 150, and 152 from the coupling units 102 and 136 and from the separators 154, 156, and 158. The plates 146, 148, 150, and 152 are thus removable from the apparatus 100.

Referring back to FIG. 2, fluid that flows from the inlet 106 to the outlet 138 does not flow only parallel to the capture surfaces, but rather some fluid flow is incidental to the capture surfaces. The capture surfaces may thus be said to form a "packed bed". Such incidental flow (which may also be referred to as "impact flow") advantageously increases diffusion of the substance and thus capture efficiency of the capture surfaces.

The coupling units 102 and 136 and the plates 146, 148, 150, and 152 are metallic in the embodiment shown, but in alternative embodiments may be glass or thermoplastic materials, for example. Also in the embodiment shown, the separators 154, 156, and 158 are thermoplastic gaskets, but in alternative embodiments may include other materials. In alternative embodiments, the apparatus 100 may be unitarily formed by etching a metallic or thermoplastic material, for example. In some embodiments, such as unitarily formed embodiments for example, the apparatus may be transparent to facilitate detection of captured substances from outside of the apparatus. Also, the plates 146, 148, 150, and 152 include capture surfaces as discussed above, but alternatively the plates 146, 148, 150, and 152 may include capture surfaces in different areas or on other sides of the plates.

The embodiment shown includes four plates 146, 148, 150, and 152 separated by three separators 154, 156, and 158, although alternative embodiments may include more or fewer plates and spacers. Also, although the plates 146 and 150 are shown having two fluid through-openings each and the plates 148 and 152 are shown having three fluid through-openings each, alternative embodiments may include more or fewer fluid through-openings in the plates. Also, although the fluid through-openings 160, 162, 172, 174, 176, 198, and 200 are elongate and rectangular, fluid through-openings in alternate embodiments may have other shapes. Further, although four threaded fasteners 120, 122, 124, and 126 are shown, alternative embodiments may include different fasteners or a different number of fasteners. Still further, the fasteners 120, 122, 124, and 126 may be omitted and the coupling units 102 and 136, the plates 146, 148, 150, and 152, and the separators 154, 156, and 158 may alternatively be held together by adhesives or clamps, for example. Also, the embodiment shown includes coupling units 102 and 136, plates 146, 148, 150, and 152, and separators 154, 156, and 158 having generally square cross-sectional shapes. However, the apparatus 100 may alternatively include such components having rectangular, circular, or other shapes, for example.

Second Embodiment

Figure 6:
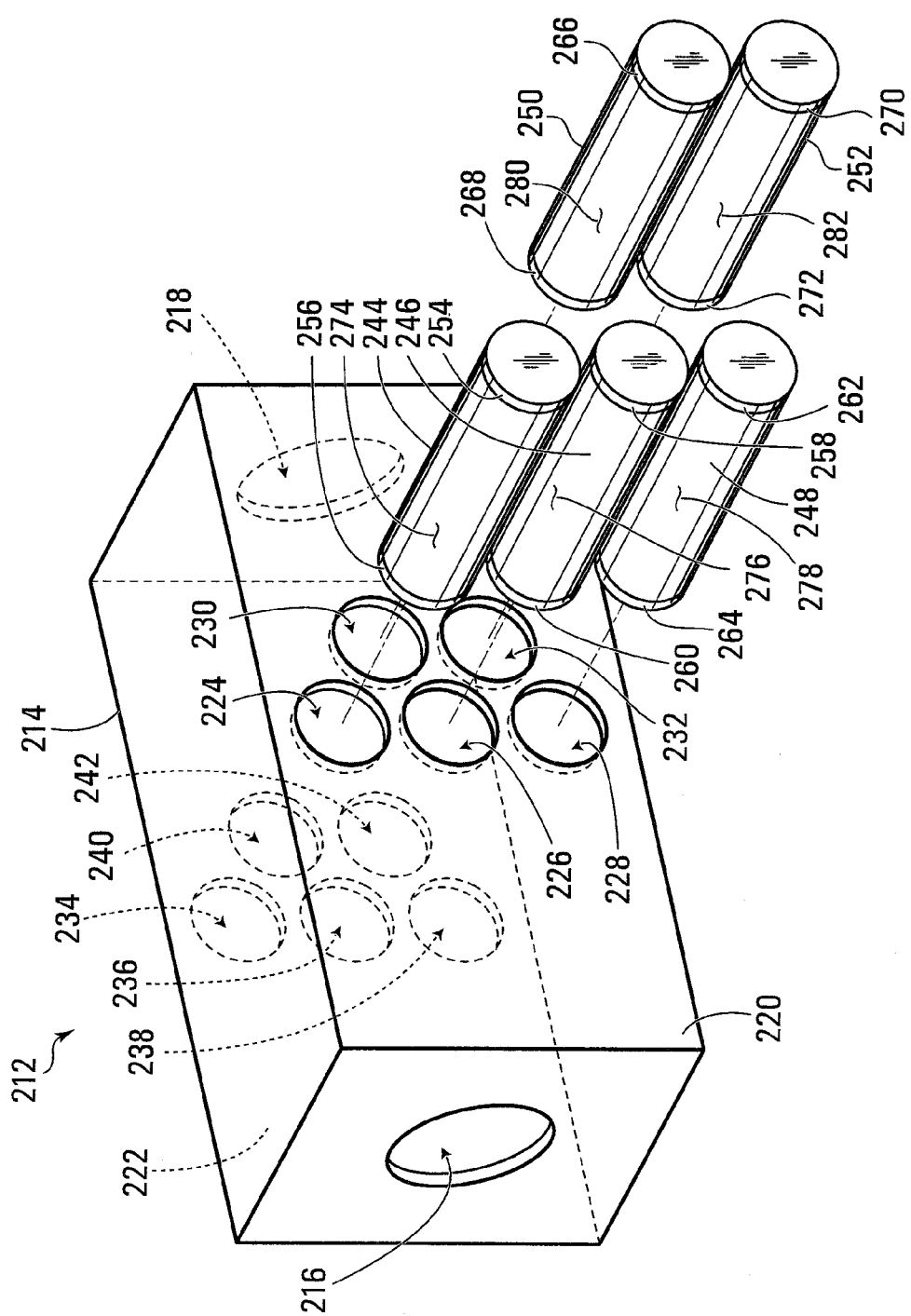
FIG. 6 is an exploded oblique view of another illustrative apparatus for determining whether a substance is carried in a fluid.

Referring to FIG. 6, another illustrative apparatus for determining whether a substance is carried in a fluid is shown generally at 212 and includes a fluid conduit 214 defining a fluid inlet shown generally at 216 and a fluid outlet shown generally at 218. The fluid conduit 214 has first and second laterally opposite walls 220 and 222 between the inlet 216 and the outlet 218. The first wall 220 defines five circular openings shown generally at 224, 226, 228, 230, and 232, and the second wall 222 defines five circular openings shown generally at 234, 236, 238, 240, and 242 laterally opposite to the circular openings 224, 226, 228, 230, and 232 respectively.

Figure 7:
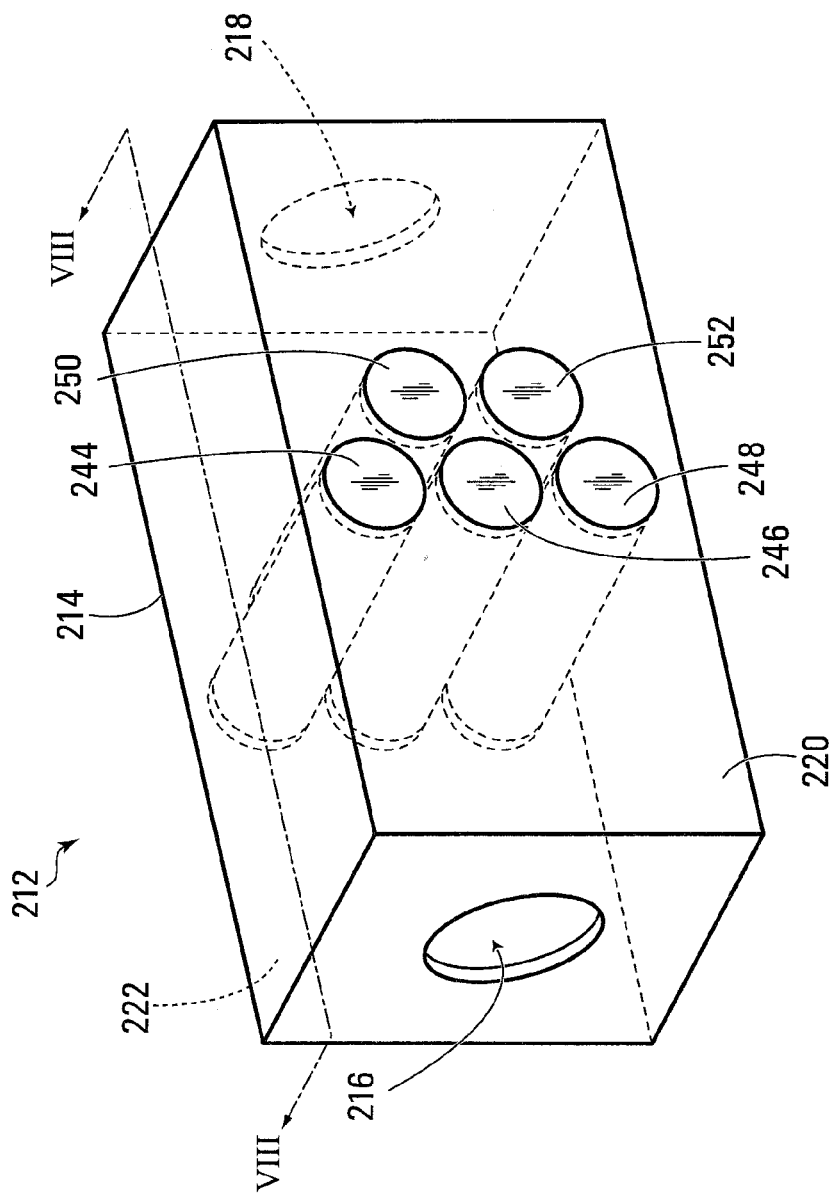
FIG. 7 is another oblique view of the apparatus of FIG. 6.

The apparatus 212 also includes five cylindrical elements 244, 246, 248, 250, and 252. The cylindrical element 244 has gaskets 254 and 256 at opposite ends thereof, the cylindrical element 246 has gaskets 258 and 260 at opposite ends thereof, the cylindrical element 248 has gaskets 262 and 264 at opposite ends thereof, the cylindrical element 250 has gaskets 266 and 268 at opposite ends thereof, and the cylindrical element 252 has gaskets 270 and 272 at opposite ends thereof. The gaskets 254, 256, 258, 260, 262, 264, 266, 268, 270, and 272 are sized and positioned to be sealingly and removably received in the circular openings 224, 234, 226, 236, 228, 238, 230, 240, 232, and 242 respectively, as shown in FIG. 7. The cylindrical elements 244, 246, 248, 250, and 252 are thus removable from the fluid conduit 214. Also, the fluid conduit 214 is thus a sealed fluid conduit between the inlet 216 and the outlet 218, and the cylindrical elements 244, 246, 248, 250, and 252 extend parallel to each other between the first and second laterally opposite walls 220 and 222.

Figure 8:
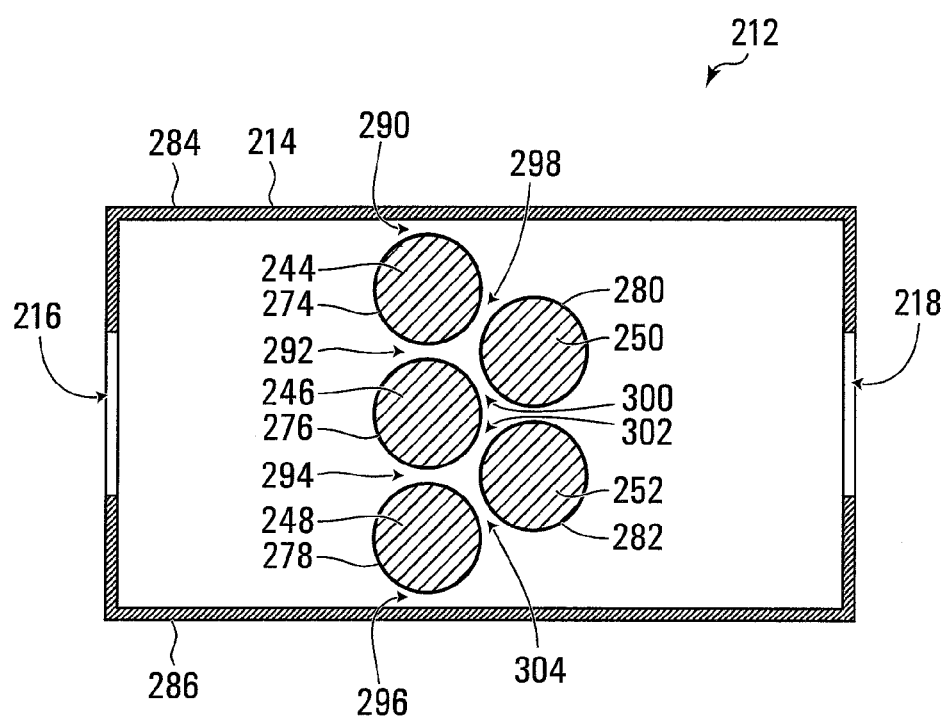
FIG. 8 is a cross-sectional view of the apparatus of FIG. 6 taken along the line VIII-VIII in FIG. 7.

Referring to FIGS. 6 and 8, the cylindrical elements 244, 246, 248, 250, and 252 have outer surfaces 274, 276, 278, 280, and 282 respectively, and some or all of those outer surfaces are capture surfaces coated with capture molecules as described above. Referring to FIG. 8, the outer surfaces 274, 276, 278, 280, and 282 are spaced apart from each other and from inner surfaces of opposite side walls 284 and 286 that extend between the first and second laterally opposite walls 220 and 222. Therefore, fluid passing through the fluid conduit 214 from the inlet 216 to the outlet 218 passes through one or more of a gap shown generally at 290 between the side wall 284 and the cylindrical element 244, a gap shown generally at 292 between the cylindrical elements 244 and 246, a gap shown generally at 294 between the cylindrical elements 246 and 248, a gap shown generally at 296 between the cylindrical element 248 and the side wall 286, a gap shown generally at 298 between the cylindrical elements 244 and 250, a gap shown generally at 300 between the cylindrical elements 246 and 250, a gap shown generally at 302 between the cylindrical elements 246 and 252, and a gap shown generally at 304 between the cylindrical elements 248 and 252.

The gaps 290, 292, 294, 296, 298, 300, 302, and 304 have minimum widths as shown in FIG. 8. The dimensions of the circular openings 224, 226, 228, 230, 232, 234, 236, 238, 240, and 242 (shown in FIG. 6), of the cylindrical elements 244, 246, 248, 250, and 252, and of the gaskets 254, 256, 258, 260, 262, 264, 266, 268, 270, and 272 (shown in FIG. 6) may be chosen so that those minimum widths have a predetermined width. The outer surfaces 274, 276, 278, 280, and 282 and the inner surfaces of the opposite side walls 284 and 286 thus guide fluid in the fluid conduit 214 to within that predetermined width of the capture surfaces on the outer surfaces 274, 276, 278, 280, and 282. As discussed above, passing the fluid over the capture surfaces consistently within that predetermined width advantageously avoids inefficiency from fluid passing over the capture surfaces at smaller or larger distances.

Referring back to FIG. 8, fluid that flows from the inlet 216 to the outlet 218 does not flow only parallel to the capture surfaces, but rather some fluid flow is incidental to the capture surfaces, and the capture surfaces may thus be said to form a "packed bed". Again, such incidental flow advantageously increases diffusion of the substance and thus capture efficiency of the capture surfaces.

The fluid conduit 214 and the cylindrical elements 244, 246, 248, 250, and 252 are metallic in the embodiment shown, but in alternative embodiments may be glass or thermoplastic materials, for example. Also in the embodiment shown, the gaskets 254, 256, 258, 260, 262, 264, 266, 268, 270, and 272 include thermoplastic material, but in alternative embodiments may include other materials. In alternative embodiments, the apparatus 212 may be unitarily formed by etching a metallic or thermoplastic material, for example. In some embodiments, such as unitarily formed embodiments for example, the apparatus may be transparent to facilitate detection of captured substances from outside of the apparatus.

The embodiment shown includes five cylindrical elements 244, 246, 248, 250, and 252, although alternative embodiments may include more or fewer cylindrical elements. Further, the embodiment shown includes the fluid conduit 214 having a generally square cross-sectional shape, but the fluid conduit 214 may alternatively have rectangular, circular, or other shapes, for example. Still further, the embodiment shown includes cylindrical elements 244, 246, 248, 250, and 252 having circular cross-sectional shapes, but the apparatus 212 may alternatively include such elements having rectangular, hexagonal, octagonal, circular, or other shapes, for example.

Third Embodiment

Figure 9:
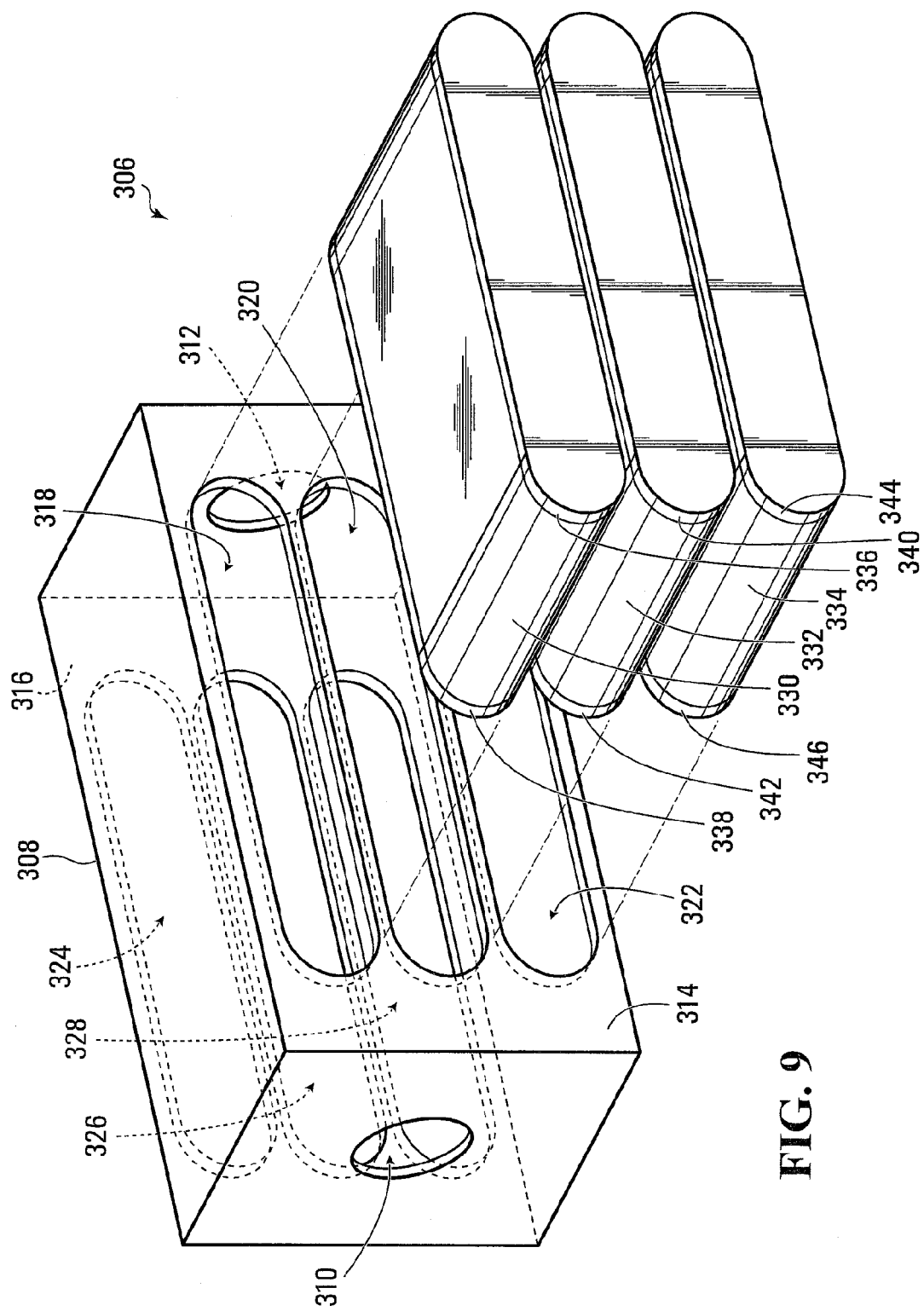
FIG. 9 is an exploded oblique view of another illustrative apparatus for determining whether a substance is carried in a fluid.

Referring to FIG. 9, another illustrative apparatus for determining whether a substance is carried in a fluid is shown generally at 306 and includes a fluid conduit 308 defining a fluid inlet shown generally at 310 and a fluid outlet shown generally at 312. The fluid conduit 308 has first and second laterally opposite walls 314 and 316 between the inlet 310 and the outlet 312. The first wall 314 defines three oblong openings shown generally at 318, 320, and 322 and extending along the first wall 314 in a direction parallel to a direction between the inlet 310 and the outlet 312. The second wall 316 defines three oblong openings shown generally at 324, 326, and 328 laterally opposite to the oblong openings 318, 320, and 322 respectively.

Figure 10:
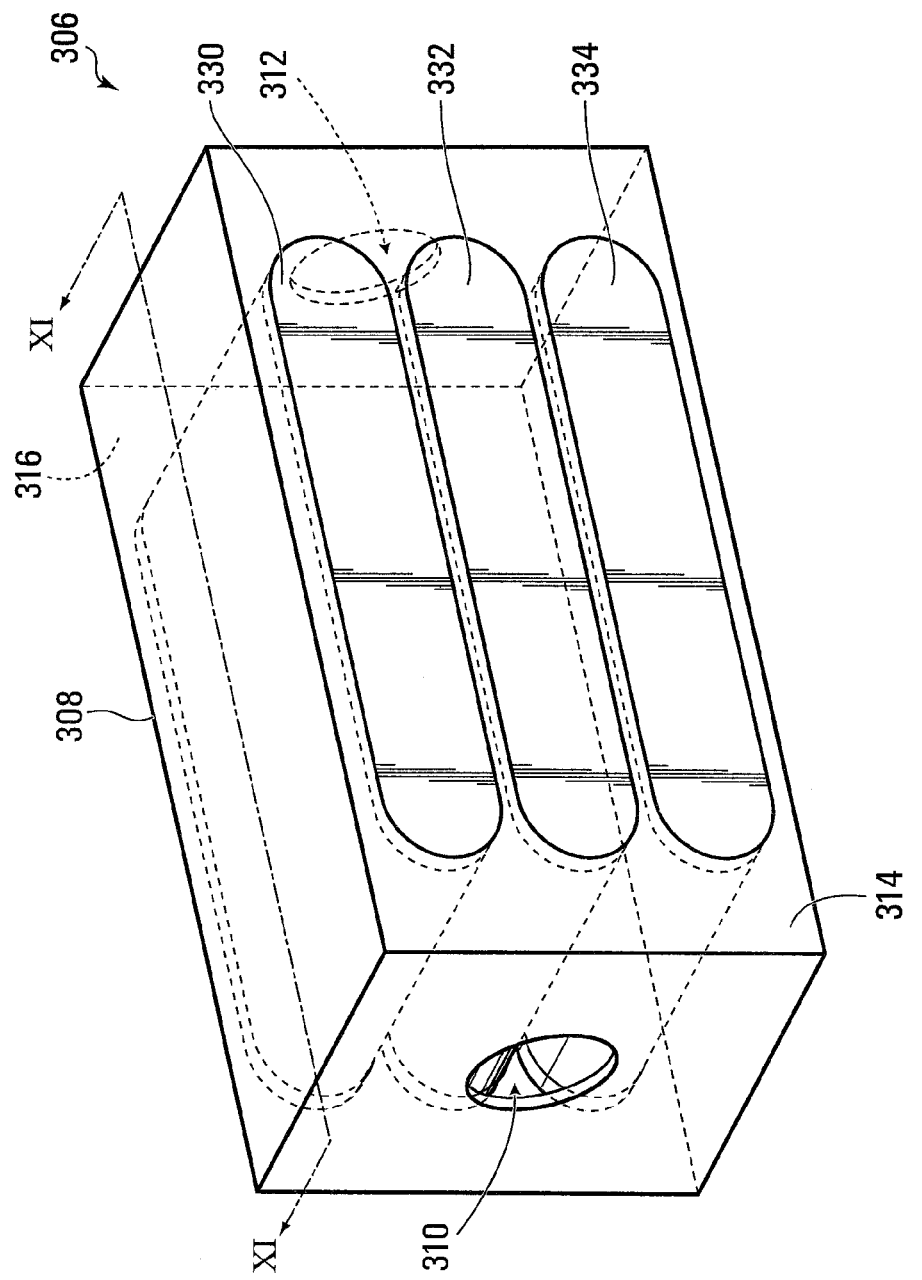
FIG. 10 is another oblique view of the apparatus of FIG. 9.

The apparatus 306 also includes three oblong elements 330, 332, and 334. The oblong element 330 has gaskets 336 and 338 at opposite ends thereof, the oblong element 332 has gaskets 340 and 342 at opposite ends thereof, and the oblong element 334 has gaskets 344 and 346 at opposite ends thereof. The gaskets 336, 338, 340, 342, 344, and 346 are sized and positioned to be sealingly and removably received in the oblong openings 318, 324, 320, 326, 322, and 328 respectively, as shown in FIG. 10. The oblong elements 330, 332, and 334 are thus removable from the fluid conduit 308. Also, the fluid conduit 308 is thus a sealed fluid conduit between the inlet 310 and the outlet 312, and the oblong elements 330, 332, and 334 extend parallel to each other between the first and second laterally opposite walls 314 and 316.

Figure 11:
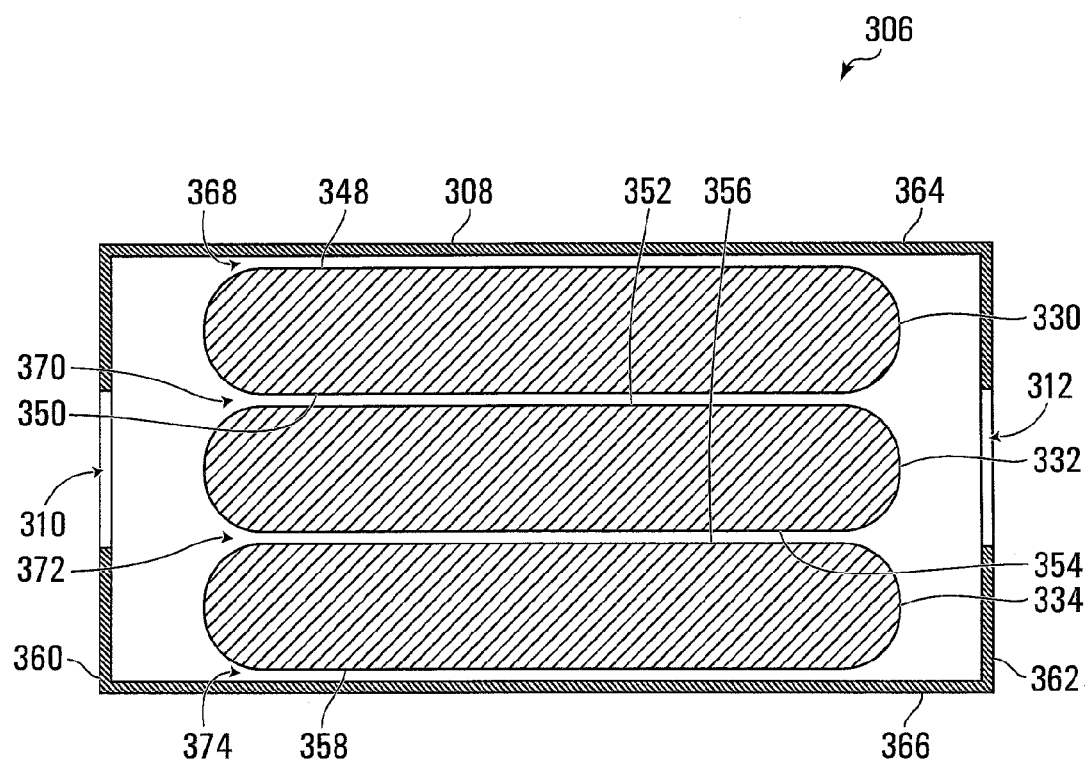
FIG. 11 is a cross-sectional view of the apparatus of FIG. 9 taken along the line XI-XI in FIG. 10.

Referring to FIG. 11, the oblong element 330 has opposed outer surfaces 348 and 350, the oblong element 332 has opposed outer surfaces 352 and 354, and the oblong element 334 has opposed outer surfaces 356 and 358.

Some or all of those outer surfaces are capture surfaces coated with capture molecules as described above. The outer surfaces 348, 350, 352, 354, 356, and 358 are spaced apart from each other and from inner surfaces of opposite side walls 360 and 362 that extend between the first and second laterally opposite walls 364 and 366. Therefore, fluid passing through the fluid conduit 308 from the inlet 310 to the outlet 312 passes through one or more of a gap shown generally at 368 between the side wall 364 and the oblong element 330, a gap shown generally at 370 between the oblong elements 330 and 332, a gap shown generally at 372 between the oblong elements 332 and 334, and a gap shown generally at 374 between the oblong element 334 and the side wall 366.

The gaps 368, 370, 372, and 374 have widths as shown in FIG. 11. The dimensions of the oblong openings 318, 320, 322, 324, 326, and 328 (shown in FIG. 9), of the oblong elements 330, 332, and 334, and of the gaskets 336, 338, 340, 342, 344, and 346 (shown in FIG. 9) may be chosen so that those widths have a predetermined width. The outer surfaces 348, 350, 352, 354, 356, and 358 and the inner surfaces of the opposite side walls 364 and 368 thus guide fluid in the fluid conduit 308 within that predetermined width of the capture surfaces on the outer surfaces 348, 350, 352, 354, 356, and 358. As discussed above, passing the fluid over the capture surfaces consistently within that predetermined width advantageously avoids inefficiency from fluid passing over the capture surfaces at smaller or larger distances.

Referring back to FIG. 11, fluid that flows from the inlet 310 to the outlet 312 does not flow only parallel to the capture surfaces, but rather some fluid flow is incidental to the capture surfaces, and the capture surfaces may thus be said to form a "packed bed". Again, such incidental flow advantageously increases diffusion of the substance and thus capture efficiency of the capture surfaces.

The fluid conduit 308 and the oblong elements 330, 332, and 334 are metallic in the embodiment shown, but in alternative embodiments may be glass or thermoplastic materials, for example. Also in the embodiment shown, the gaskets 336, 338, 340, 342, 344, and 346 include thermoplastic material, but in alternative embodiments may include other materials. In alternative embodiments, the apparatus 306 may be unitarily formed by etching a metallic or thermoplastic material, for example. In some embodiments, such as unitarily formed embodiments, the apparatus may be transparent to facilitate detection of captured substances from outside of the apparatus.

The embodiment shown includes three oblong elements 330, 332, and 334, although alternative embodiments may include more or fewer oblong elements. Further, the embodiment shown includes the fluid conduit 308 having a generally square cross-sectional shape, but the fluid conduit 308 may alternatively have rectangular, circular, or other shapes, for example. Still further, the embodiment shown includes oblong elements 330, 332, and 334, but the apparatus 306 may alternatively include such elements having other shapes cross-sectional shapes.

Fourth Embodiment

Figure 12:
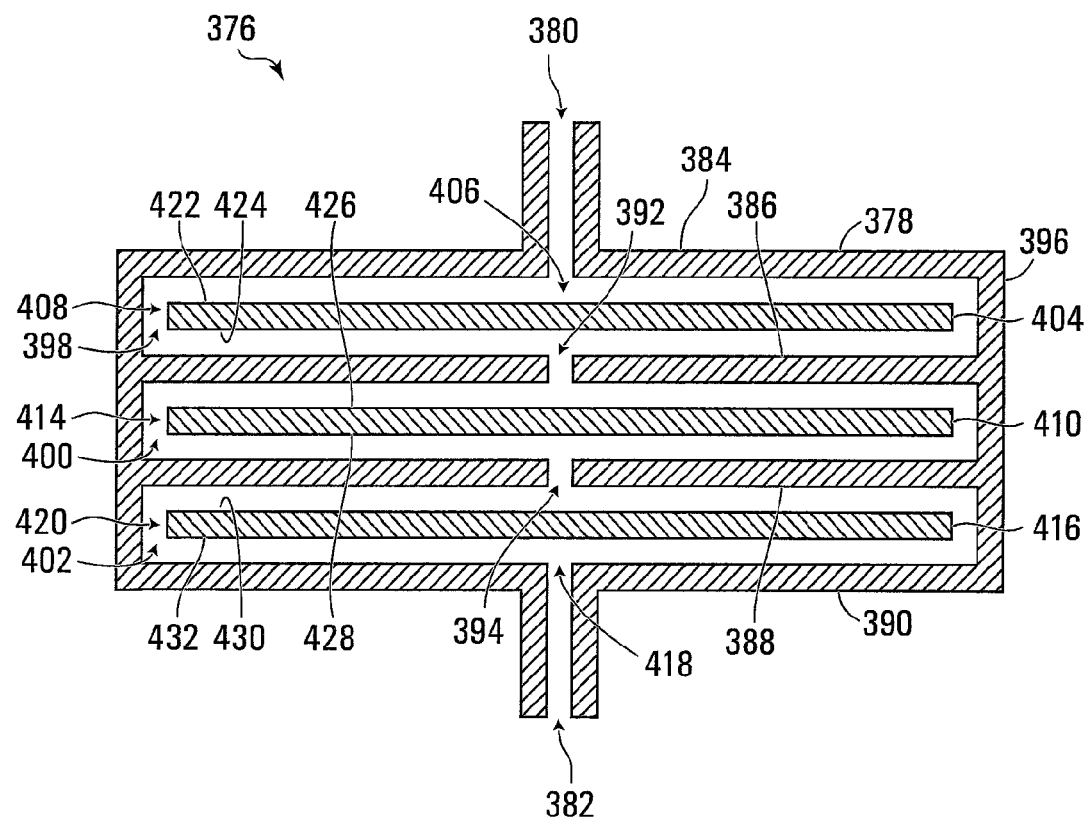
FIG. 12 is a cross-sectional view of another illustrative apparatus for determining whether a substance is carried in a fluid.

Referring to FIG. 12, another illustrative apparatus for determining whether a substance is carried in a fluid is shown generally at 376 and includes a fluid conduit 378 defining a fluid inlet shown generally at 380 and a fluid outlet shown generally at 382. The fluid conduit 378 includes first, second, third, and fourth longitudinally spaced-apart annular walls 384, 386, 388, and 390. The first annular wall 384 surrounds the inlet 380. The second and third annular walls 386 and 388 surround respective openings shown generally at 392 and 394. The fourth annular wall 390 surrounds the outlet 382. The inlet 380, outlet 382, and openings 392 and 394 are aligned along an axis of the fluid conduit 378.

The fluid conduit 378 also includes a fifth annular wall 396 surrounding and the adjacent first, second, third, and fourth longitudinally spaced-apart annular walls 384, 386, 388, and 390. Thus the first, second, and fifth annular walls 384, 386, and 396 define a first cylindrical region shown generally at 398, the second, third, and fifth annular walls 386, 388, and 396 define a second cylindrical region shown generally at 400, and the third, fourth, and fifth annular walls 388, 390, and 396 define a third cylindrical region shown generally at 402. The first region 398 is in fluid communication with the inlet 380. The first and second regions 398 and 400 are in fluid communication through the opening 392. The second and third regions 400 and 402 are in fluid communication through the opening 394. The third region 402 is in fluid communication with the outlet 382.

The apparatus 376 also includes a first cylindrical element 404 removably positioned in the first region 398 and spaced apart from the first and second annular walls 384 and 386. The first cylindrical element 404 has a center shown generally at 406 proximate the inlet 380 and opening 392, and a peripheral region shown generally at 408 proximate the fifth annular wall 396. The apparatus 376 also includes a second cylindrical element 410 removably positioned in the second region 400 and spaced apart from the second and third annular walls 386 and 388. The second cylindrical element 410 has a center shown generally at 412 proximate the openings 392 and 394, and a peripheral region shown generally at 414 proximate the fifth annular wall 396. The apparatus 376 also includes a third cylindrical element 416 removably positioned in the third region 402 and spaced apart from the third and fourth annular walls 388 and 390. The third cylindrical element 416 has a center shown generally at 418 proximate the opening 394 and outlet 382, and a peripheral region shown generally at 420 proximate the fifth annular wall 396.

Fluid received at the inlet 380 contacts a first circular surface 422 of the first cylindrical element 404 and flows generally radially outward along the first circular surface 422 from the center 406 to the peripheral region 408 of the first cylindrical element 404. The fluid then passes to a second circular surface 424 opposite the first circular surface 422 and flows generally radially inward along the second circular surface 424 from the peripheral region 408 to the center 406 of the first cylindrical element 404, and then through the opening 392. Fluid flows in substantially the same manner around first and second opposite circular surfaces 426 and 428 of the second cylindrical element 410, through the opening 394, around first and second opposite circular surfaces 430 and 432 of the third cylindrical element 416, and out the outlet 382.

Some or all of the circular surfaces 422, 424, 426, 428, 430, and 432 are capture surfaces coated with capture molecules as described above. Therefore, when fluid passes from the inlet 380 to the outlet 382, such fluid passes over the capture surfaces on the circular surfaces 422, 424, 426, 428, 430, and 432, and adjacent surfaces of the annular walls 384, 386, 388, and 390 guide the fluid to within a predetermined distance of the capture surfaces. Again, passing fluid over such capture surfaces consistently at that predetermined distance advantageously avoids inefficiency from fluid passing over the capture surfaces at smaller or larger distances.

Fluid that flows from the inlet 380 to the outlet 382 does not flow only parallel to the capture surfaces, but rather some fluid flow is incidental to the capture surfaces, and the capture surfaces may thus be said to form a "packed bed". Again, such incidental flow advantageously increases diffusion of the substance and thus capture efficiency of the capture surfaces.

The fluid conduit 378 and the cylindrical elements 404, 410, and 416 are metallic in the embodiment shown, but in alternative embodiments may be glass or thermoplastic materials, for example. In some embodiments, such as unitarily formed embodiments, the apparatus may be transparent to facilitate detection of captured substances from outside of the apparatus. Also, the embodiment shown includes three cylindrical elements 404, 410, and 416, although alternative embodiments may include more or fewer cylindrical elements. Further, in the embodiment shown, the fluid conduit 378 and the cylindrical elements 404, 410, and 416 are generally axially symmetric, but the fluid conduit 378 and the cylindrical elements 404, 410, and 416 may alternatively have rectangular or other cross-sectional shapes, for example.

Electric Field

In the embodiments described above, capture of the substance on the capture surfaces may be facilitated by applying an electric field around the capture surfaces. For example, referring to FIG. 13, an illustrative capture assembly is shown generally at 434 and includes a first metallic plate 436 having a capture surface 438. As discussed above, the capture surface 438 is coated with a plurality of capture molecules (not shown). The first metallic plate 436 is electrically grounded at 440.

The capture assembly 434 also includes a second metallic plate 442 having a fluid guiding surface 444. The fluid guiding surface 444 guides fluid in a region 446 between the capture surface 438 and the fluid guiding surface 444, and the fluid guiding surface 444 is a predetermined distance from the capture surface 438 to guide the fluid within the predetermined distance from the capture surface 438.

Figure 13:
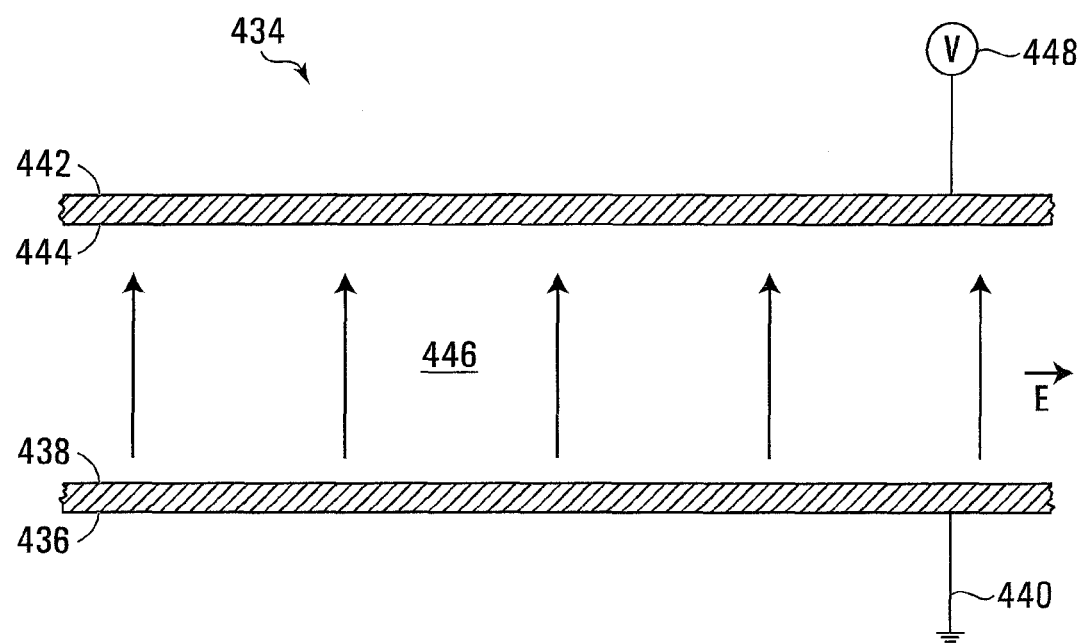
FIG. 13 is a schematic illustration of an illustrative capture assembly.

The second metallic plate 442 is electrically coupled to a voltage source 448, which provides a negative voltage to the second metallic plate 442. The fluid and other substances in the region 446 are generally dielectric, and therefore the first and second metallic plates 436 and 442 function as a capacitor to generate an electric field (shown as $\vec{E}$ in FIG. 13) in the region 446. If substances in the fluid have an electrophoretic mobility $\mu_e$, then for a relatively flow Reynolds number, the electric field $\vec{E}$ imparts a velocity $\vec{v}$ to the substances given by $\vec{v}=\mu_e\vec{E}$. The electric field $\vec{E}$ thus facilitates capture of substances in the fluid on the capture surface 438, and thus when compared to a capture assembly without the electric field $\vec{E}$, the electric field $\vec{E}$ may advantageously increase capture efficiency of the capture surface 438. The electric field $\vec{E}$ may also advantageously permit a greater distance between the capture surface 438 and the fluid guiding surface 444 to enable a greater rate of fluid flow through the region 446. Any or all of the capture surfaces and fluid guiding surfaces discussed above and illustrated in FIGS. 1 to 12 may advantageously be modified to include such an electric field as shown in FIG. 13.

Although the capture assembly 434 in the embodiment shown includes first and second metallic plates 436 and 442, alternative embodiments may include other conductors or materials capable of generating an electric field.

Also, although the voltage source 448 provides a negative voltage to the second metallic plate 442, voltage sources in other embodiments may include voltage sources for alternating current or other voltage sources, for example.

Numerical Models

Flow of a fluid through an apparatus, such one of the apparatuses described above, may be predicted with numerical models. One such numerical model is described by Sina Jomeh and Mina Hoorfar in *Numerical Modeling of Mass Transport in Microfluidic Biomolecule-Capturing Devices Equipped with Reactive Surfaces* published in *Chemical Engineering Journal* 165 (2010) at 668-677 and in *Numerical Investigation of the Effect of Geometric and Physiochemical Parameters on Biomolecule Capture Efficiency* published in *Proceedings of the ASME* 2010 *3rd Joint US-European Fluids Engineering Summer Meeting and 8th International Conference on Nanochannels, Microchannels, and Minichannels*, both of which are incorporated herein by reference. In that model, two-dimensional incompressible Navier-Stokes equations and the continuity equation provide that $$\nabla \cdot u = 0$$

and $$\rho u \cdot \nabla u = -\nabla p + \mu \nabla^2 u$$

where u is velocity of the fluid, p is pressure, $\rho$ is the density of the fluid, and $\mu$ is the dynamic viscosity of the fluid.

At a steady state of flow, the fluid enters an inlet of an apparatus carrying a substance at an initial concentration $C_0$. Where D is the diffusion coefficient of the substance, the transient two-dimensional mass transport equation provides that $$\frac{\partial C}{\partial t} + u \cdot \nabla C = D \nabla^2 C.$$

where C is the concentration of the substance.

The substance carried by the fluid reacts at detection boundaries of the apparatus with forward and backward reaction rates of $k_{on}$ and $k_{off}$ respectively. If the detection boundaries have an initial concentration $C_{s0}$ of capture molecules, a concentration of $C_s$ of the substance is captured at the detection boundaries, and the substance has a concentration $C_{wall}$ at the detection boundaries, then $$\frac{\partial C_s}{\partial t} = k_{on} C_{wall}(C_{s0} - C_s) - k_{off} C_s.$$

At an outlet of the apparatus, convective flux is specified as $$n(-D\nabla C) = 0$$

where n is a vector normal to the boundary. All other boundaries of the apparatus are assumed to be insulated or symmetric, meaning that $$n \cdot (-D\nabla C + Cu) = 0.$$

The foregoing equations may be expressed in dimensionless forms as $$\frac{\partial C^*}{\partial t^*} + \left( u^* \frac{\partial C^*}{\partial x^*} + v^* \frac{\partial C^*}{\partial y^*} \right) = \frac{1}{Pe^2} \frac{\partial^2 C^*}{\partial x^{*2}} + \frac{\partial^2 C^*}{\partial y^{*2}}$$

and $$\frac{\partial C_s^*}{\partial t^*} = \varepsilon Da[C_{wall}^*(1 - C_s^*) - K_D C_s^*]$$

where $u^* \equiv \frac{u}{u_{avg}}, v^* \equiv \frac{v}{u_{avg}}, C^* \equiv \frac{C}{C_0}, C_s^* \equiv \frac{C_s}{C_{s0}}$, Further, in the dimensionless equations above, $$x^* \equiv \frac{X}{hPe} \text{ and } y^* \equiv \frac{y}{t}$$

are dimensionless coordinates, $$t^* \equiv \frac{Dt}{h^2}$$

is dimensionless time, h is a characteristic length or flow path width, $u_{avg}$ is average inlet velocity of the fluid, Pe is a Peclet number, Da is a Damkohler number, $\in$ is the relative adsorption capacity, and $K_D$ is the equilibrium dissociation constant.

In this model, effectiveness of an apparatus may be measured by capture efficiency defined as $$CE \equiv 1 - C^*_{b,outlet}$$

where $C^*_{b,outlet}$ is the non-dimensional form of the bulk concentration at the outlet and is defined as $$C^*_{b,outlet} \equiv \frac{1}{C_0 u_{avg} h} \int_0^h C_{outlet} u_{outlet} dy.$$

Figure 14:
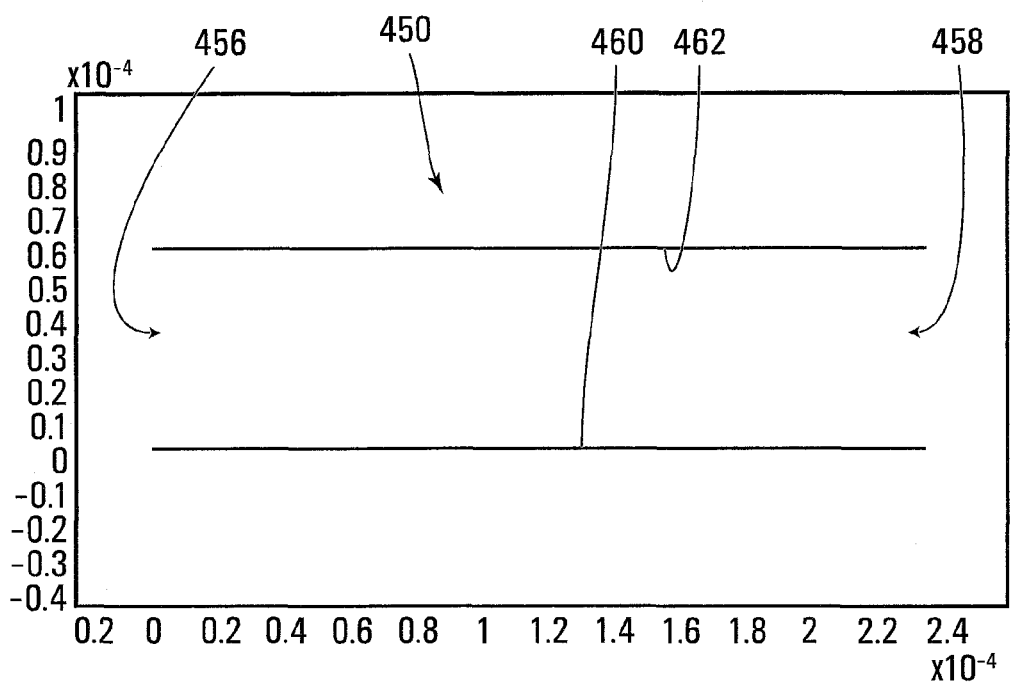
FIG. 14 is a schematic illustration of a first illustrative model apparatus.
Figure 15:
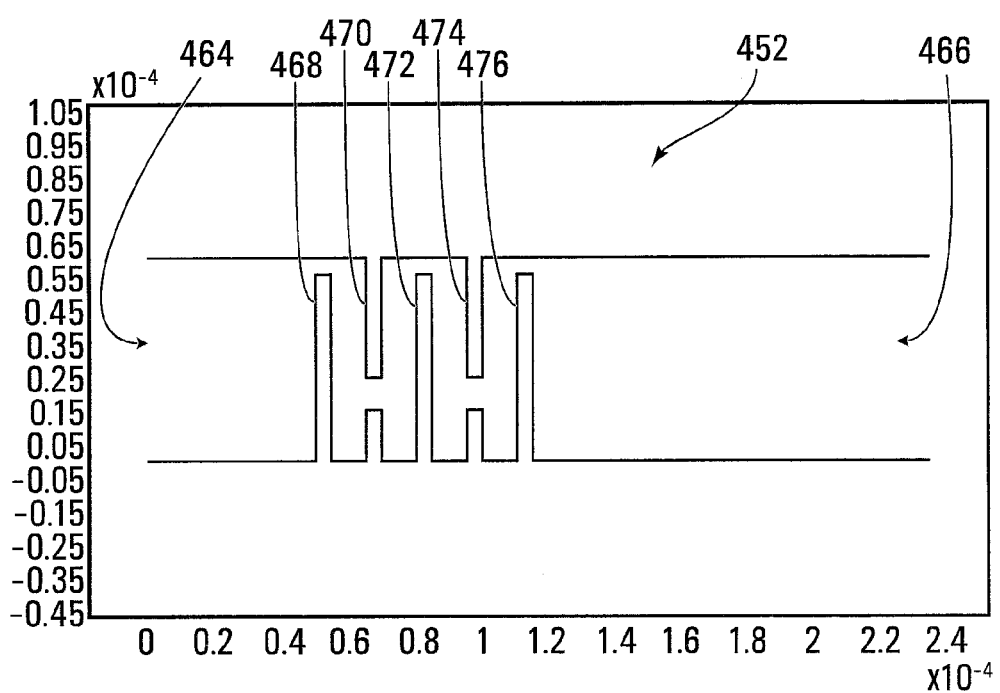
FIG. 15 is a schematic illustration of a second illustrative model apparatus.
Figure 16:
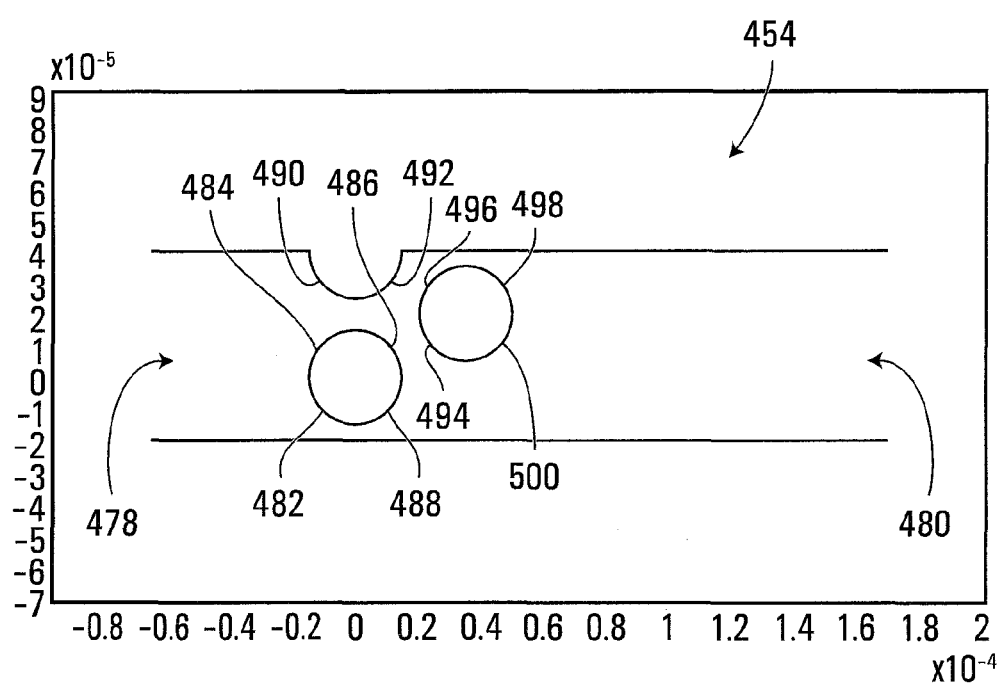
FIG. 16 is a schematic illustration of a third illustrative model apparatus.

To illustrate some advantages of apparatuses such as those discussed above, the aforementioned model has been numerically applied to a first illustrative model apparatus shown generally at 450 in FIG. 14, a second illustrative model apparatus shown generally at 452 in FIG. 15, and a third illustrative model apparatus shown generally at 454 in FIG. 16. The dimensions shown in FIGS. 14, 15, and 16 are in meters.

The numerical model was applied with the following parameter values:

| Parameter | Value |
| --- | --- |
| Forward reaction rate ($k_{on}$) | 105 m³/(mol s) |
| Backward reaction rate ($k_{off}$) | $10^{-2}$ s⁻¹ |
| Ligand concentration ($C_{s0}$) | $10^{-8}$ mol/m² |
| Diffusion coefficient (D) | $10^{-11}$ m²/s |
| Inlet concentration ($C_0$) | $10^{-6}$ mol/m³ |
| Average inlet velocity ($u_{avg}$) | $10^{-4}$ m/s |
| Peclet number (Pe) | 100 |
| Damkohler number (Da) | 1000 |
| Relative adsorption capacity ($\epsilon$) | 0.01 |
| Equilibrium dissociation constant ($K_D$) | 0.1 |

Referring to FIG. 14, the first model apparatus 450 includes an inlet shown generally at 456, an outlet shown generally at 458, a capture surface 460 extending between the inlet 456 and the outlet 458, and another surface 462 opposite the capture surface 460. In the first model apparatus 450, fluid simply passes between the surfaces 460 and 462 when flowing from the inlet 456 to the outlet 458.

Referring to FIG. 15, the second model apparatus 452 includes an inlet shown generally at 464, an outlet shown generally at 466, and five capture surfaces 468, 470, 472, 474, and 476 as shown in FIG. 15. The second model apparatus 452 therefore includes capture surfaces similar to those discussed above in the apparatus 100 illustrated in FIGS. 1 and 2.

Referring to FIG. 16, the third model apparatus 454 includes an inlet shown generally at 478, an outlet shown generally at 480, and ten capture surfaces 482, 484, 486, 488, 490, 492, 494, 496, 498, and 500, each extending over a respective 90° circular arc as shown in FIG. 16. The third model apparatus 454 therefore includes capture surfaces similar to those discussed above in the apparatus 212 illustrated in FIGS. 6, 7, and 8.

In the model described above, a concentration of $C_s$ of the substance is captured at detection boundaries. Therefore, predictions of $C_s$ over the various detection surfaces of the second and third model apparatuses 452 and 454 may facilitate identifying locations where capture surfaces may be ideally positioned in the apparatuses 100 and 212 discussed above.

Figure 17:
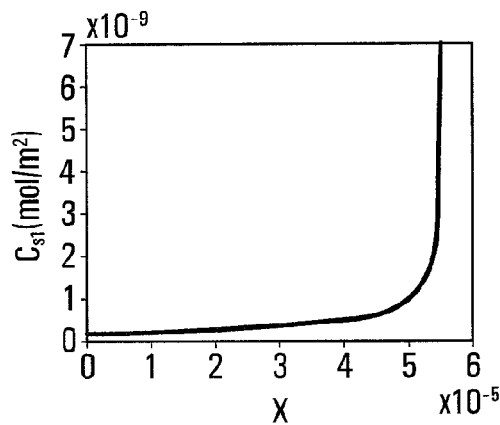
FIGS. 17 to 21 are illustrations numerical predictions of concentrations of a substance over the capture surfaces of the model apparatus of FIG. 15.
Figure 18:
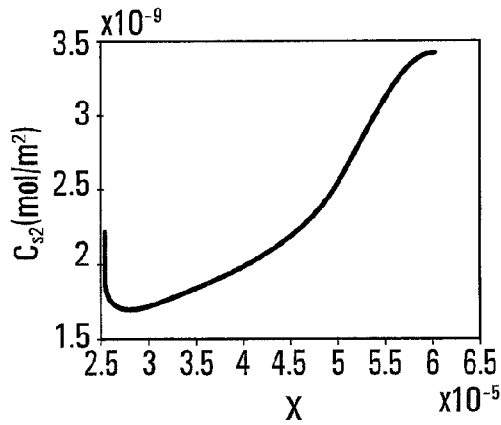
Figure 19:
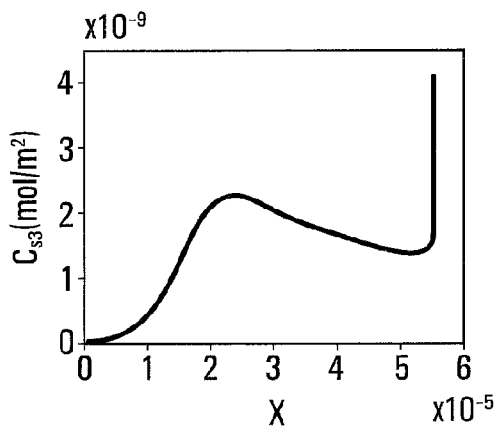
Figure 20:
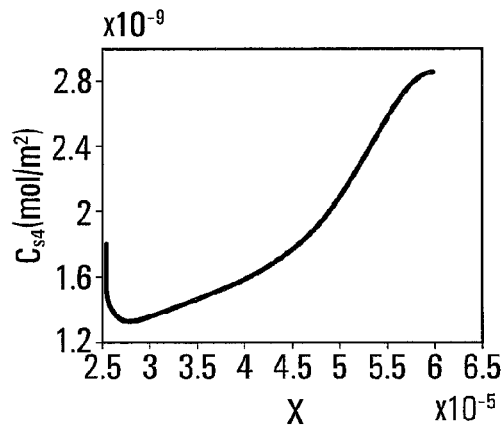
Figure 21:
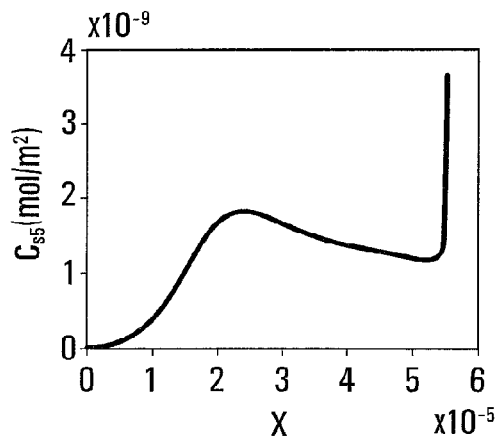

Referring to FIGS. 15 and FIGS. 17 to 21: FIG. 17 illustrates numerical predictions of $C_{s1}$, namely concentration of the substance over the capture surface 468; FIG. 18 illustrates numerical predictions of $C_{s2}$, namely concentration of the substance over the capture surface 470; FIG. 19 illustrates numerical predictions of $C_{s3}$, namely concentration of the substance over the capture surface 472; FIG. 20 illustrates numerical predictions of $C_{s4}$, namely concentration of the substance over the capture surface 474; and FIG. 21 illustrates numerical predictions of $C_{s5}$, namely concentration of the substance over the capture surface 476.

Figure 22:
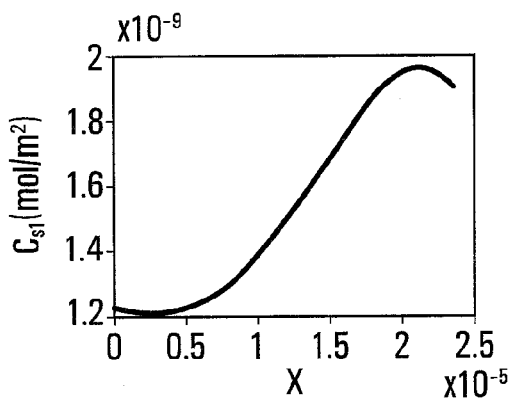
FIGS. 22 to 31 are illustrations numerical predictions of concentrations of a substance over the capture surfaces of the model apparatus of FIG. 16.
Figure 23:
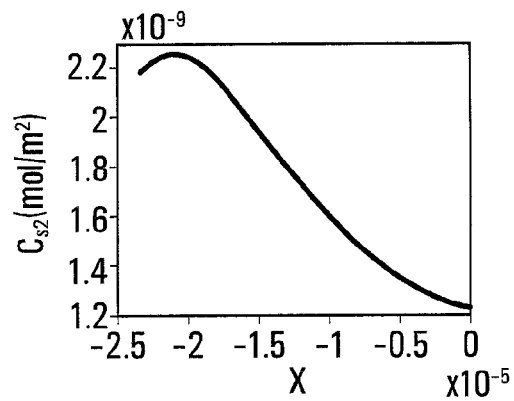
Figure 24:
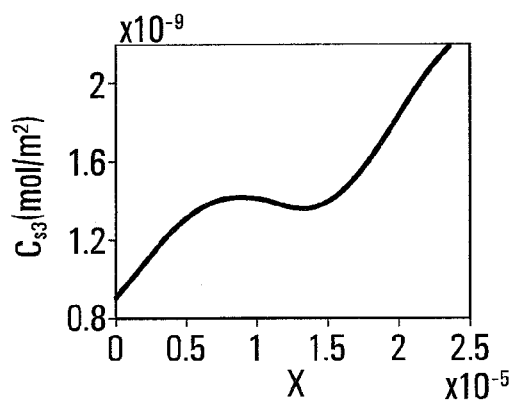
Figure 25:
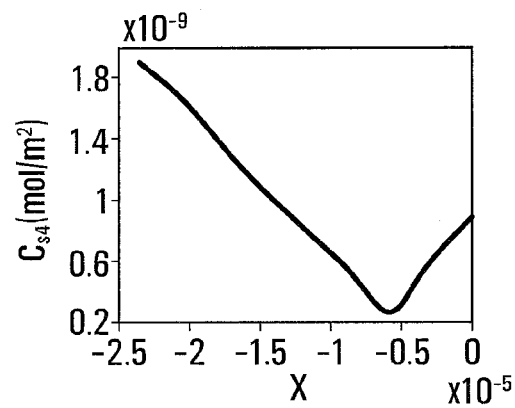
Figure 26:
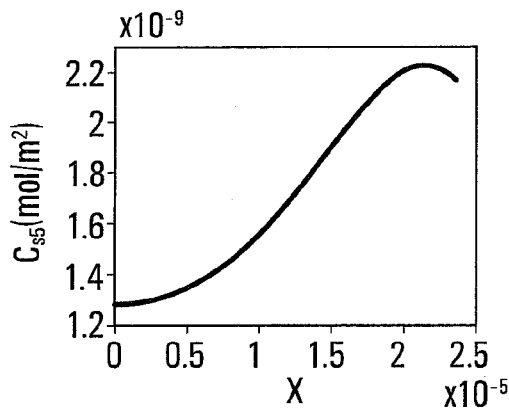
Figure 27:
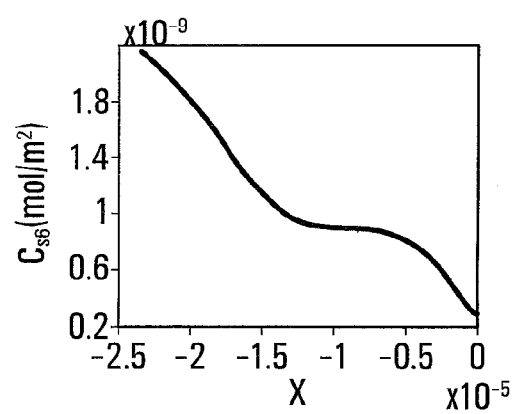
Figure 28:
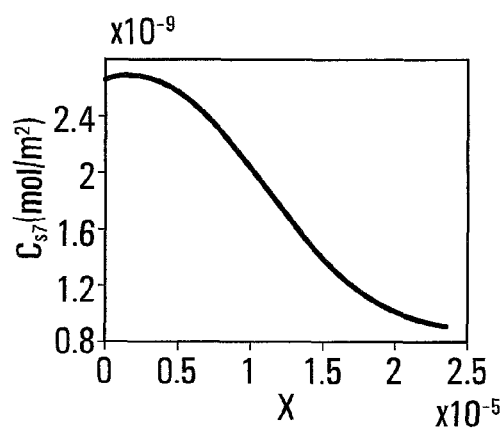
Figure 29:
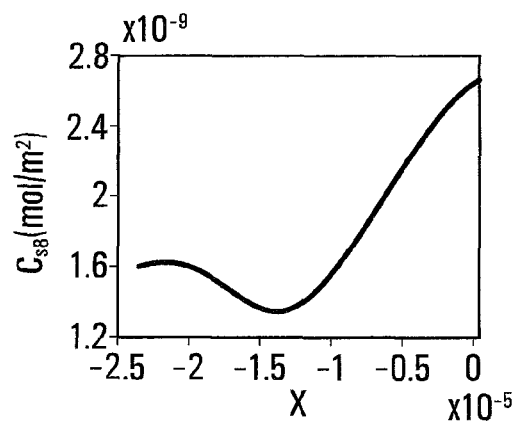
Figure 30:
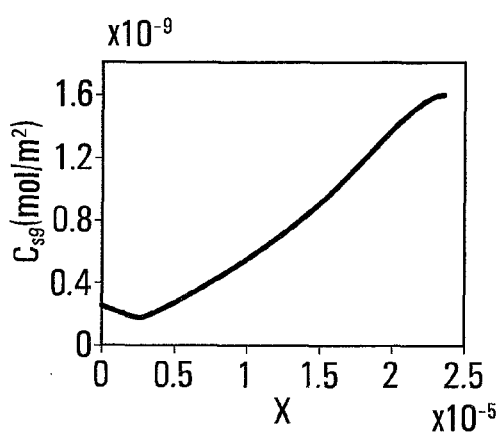
Figure 31:
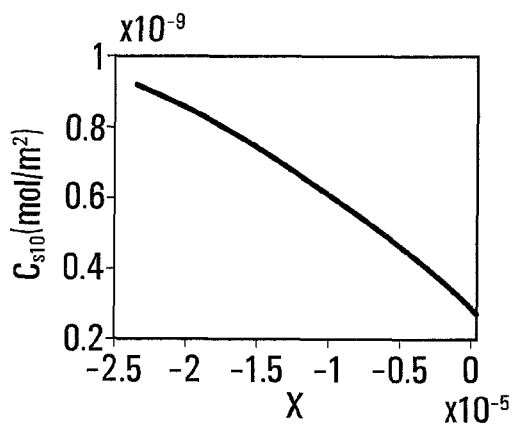

Also, referring to FIGS. 16 and FIGS. 22 to 31: FIG. 22 illustrates numerical predictions of $C_{s1}$, namely concentration of the substance over the capture surface 482; FIG. 23 illustrates numerical predictions of $C_{s2}$, namely concentration of the substance over the capture surface 484; FIG. 24 illustrates numerical predictions of $C_{s3}$, namely concentration of the substance over the capture surface 486; FIG. 25 illustrates numerical predictions of $C_{s4}$, namely concentration of the substance over the capture surface 488; FIG. 26 illustrates numerical predictions of $C_{s6}$, namely concentration of the substance over the capture surface 490; FIG. 27 illustrates numerical predictions of $C_{s6}$, namely concentration of the substance over the capture surface 492; FIG. 28 illustrates numerical predictions of $C_{s7}$, namely concentration of the substance over the capture surface 494; FIG. 29 illustrates numerical predictions of $C_{s8}$, namely concentration of the substance over the capture surface 496; FIG. 30 illustrates numerical predictions of $C_{s9}$, namely concentration of the substance over the capture surface 498; and FIG. 31 illustrates numerical predictions of $C_{s10}$, namely concentration of the substance over the capture surface 500.

As indicated above, capture surfaces may be positioned on surfaces where numerical predictions of $C_s$ are higher in order to improve efficiency of the capture surfaces per unit area of the capture surfaces.

Figure 32:
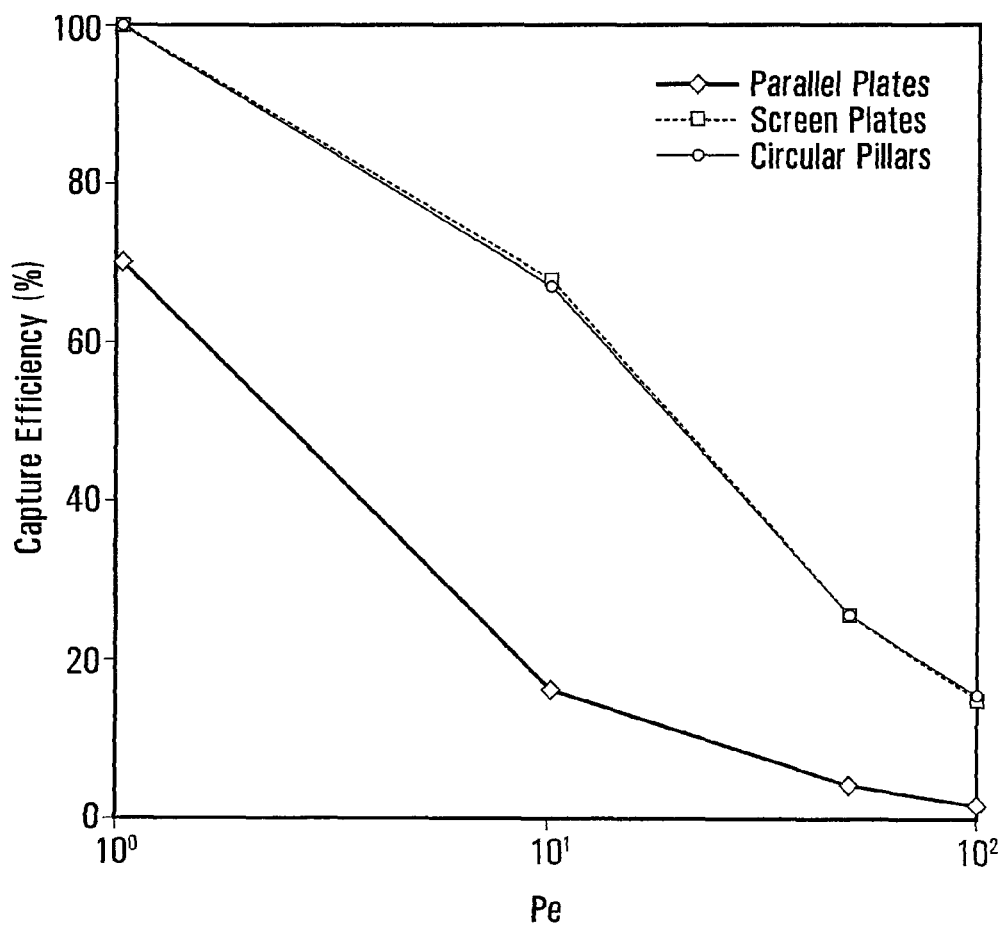
FIG. 32 is an illustration of numerical predictions of capture efficiency of capture surfaces of the model apparatuses of FIGS. 15, 16, and 17.

Referring to FIG. 32, numerical predictions of capture efficiency (CE), at various Peclet numbers, are illustrated for the first model apparatus 450 (shown in FIG. 14) with diamond-shaped points, for the second model apparatus 452 (shown in FIG. 15) with square-shaped points, and for the third model apparatus 454 (shown in FIG. 16) with circle-shaped points. The numerical predictions illustrated in FIG. 32 show that over the various Peclet numbers, the second and third model apparatuses 452 and 454 are predicted to have greater capture efficiency than the first model apparatus 450. Accordingly, it is believed that the apparatuses discussed above provide for improved capture efficiency when compared to apparatuses such as the first model apparatus 450.

The model described above may be used to test different parameters, such as average inlet velocity $u_{avg}$ and characteristic length h, for example, to identify preferably such parameters for a particular fluid for or particular reaction rates of a substance to be captured. The model may also be used to test different variations of the apparatus described above, such as variation in shape and number of surfaces, to identify preferable such variations.

Detection

Figure 33:
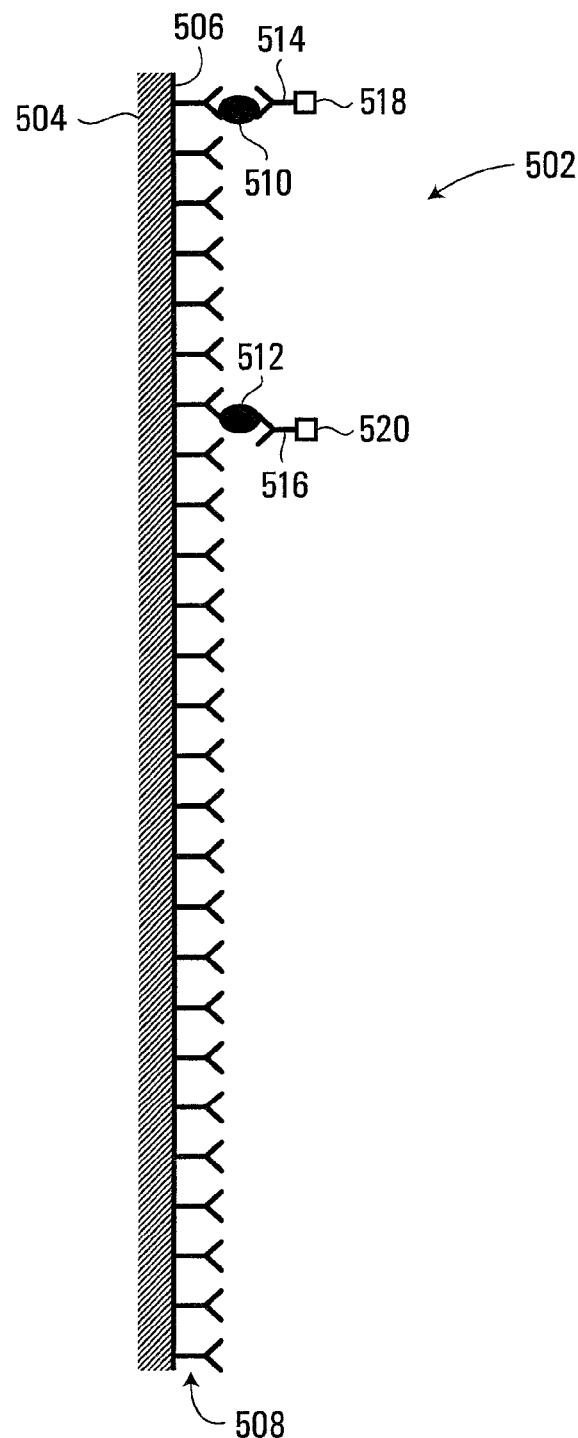
FIG. 33 is a schematic illustration of another illustrative capture assembly.

Referring to FIG. 33, an illustrative capture assembly 502 includes a metallic plate 504 having a capture surface 506. As discussed above, the capture surface 506 is coated with a plurality of capture molecules, which in the embodiment shown are antibodies shown generally at 508. Alternative embodiments may include other capture molecules. In the embodiment shown, two pathogens 510 and 512 were carried by water past the capture surface 506 and bonded to respective antibodies 508. Alternative embodiments may include other detected substances, such as other protozoans, bacteria, viruses, or chemical contaminants, for example.

To detect the pathogens 510 and 512, the metallic plate 504 is subjected to a plurality of capture molecules including capture molecules 514 and 516. Such capture molecules again having binding affinities with the substance. Again, such capture molecules may be identified by one skilled in the art depending on the substance to be captured. In general, such capture molecules may include, for example, proteins such as antibodies, antibody fragments, lectins, or protein aptamers, or nucleic acids such as nucleic acid aptamers. For example, the antibodies may include one or more of IgG, IgA, IgE, or IgM forms, and the antibody fragments may include one or more of Fab', F(ab')$_2$, and Fab forms. In the embodiment shown, the capture molecule 514 is bonded to the pathogen 510, and the capture molecule 515 is bonded to the pathogen 512.

Figure 34:
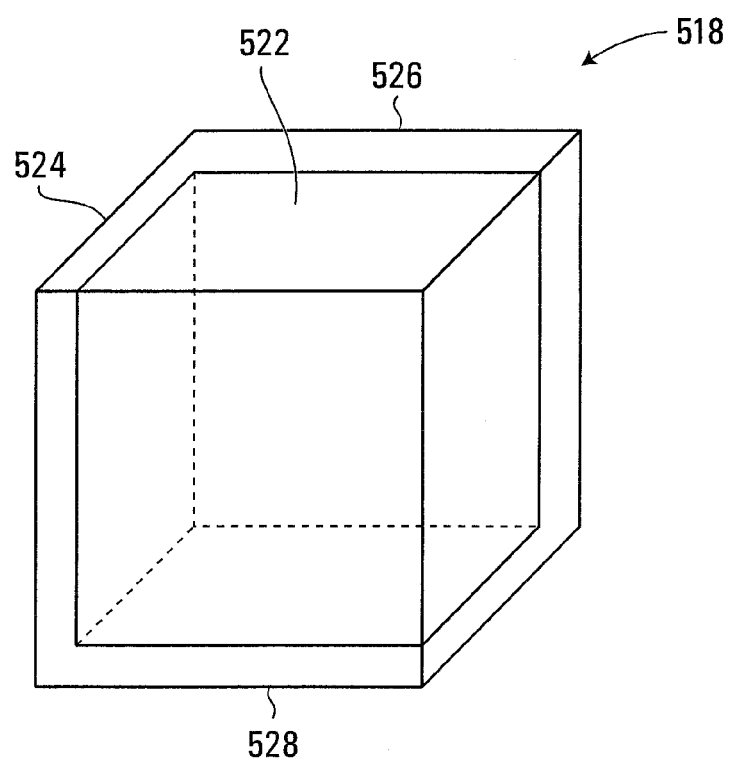
FIG. 34 is an oblique view of a microretroreflector shown in FIG. 33.
Figure 35:
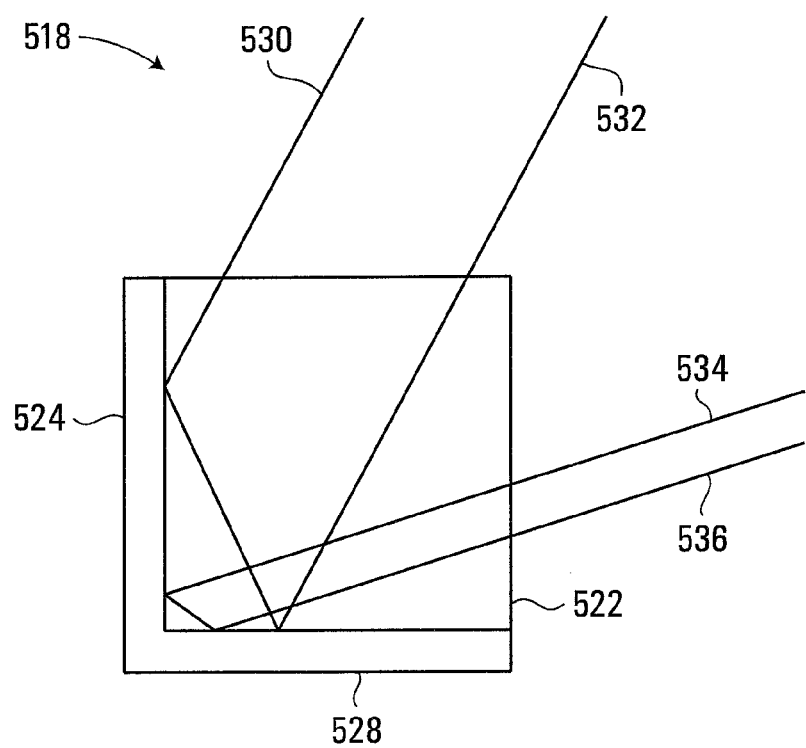
FIG. 35 is a side view of the microretroreflector shown in FIG. 34.

The capture molecules 514 and 516 in the embodiment shown are bonded to respective microretroreflectors 518 and 520 before being subjected to the capture surface 506. Referring to FIGS. 34 and 35, the microretroreflector 518 includes a generally transparent cubic portion 522 having three mutually orthogonal reflectors 524, 526, and 528 on respective adjacent faces. Thus, referring to FIG. 35, a first incident light beam 530 reflects back from the reflectors 524 and 528 in a first reflected light beam 532 that is generally parallel to the first incident light beam 530. Further, a second incident light beam 534 nonparallel to the first incident light beam 530 also reflects back from the reflectors 524 and 528 in a second reflected light beam 536 that is generally parallel to the second incident light beam 534. The microretroreflector 518 is thus an efficient reflector of light from various incident angles. More generally, microretroreflectors and some method of their manufacture are discussed in United States Patent Publication No. 2006/0088946 entitled OPTICAL MICROLABELS: SHAPES AND REFLECTORS and published Apr. 27, 2006, which is incorporated herein by reference.

Referring back to FIG. 33, the capture molecules 514 and 516 advantageously indicate the presence of the pathogens 510 and 512 by being previously bound to the reflectors 518 and 520 respectively, and by binding to the pathogens 510 and 512. Thus, a quantity of light reflected from a portion of the capture surface 506 after exposing the capture surface 506 to capture molecules such as the capture molecules 514 and 516 may be proportional to a concentration of the pathogens on that portion of the capture surface 506.

Although the embodiment shown includes microretroreflectors 518 and 520, in alternative embodiments, the capture molecules may include other reflectors, or fluorescent molecules, for example. Such microretroreflectors and fluorescent molecules may generally and collectively be referred to as "signalers".

Figure 36:
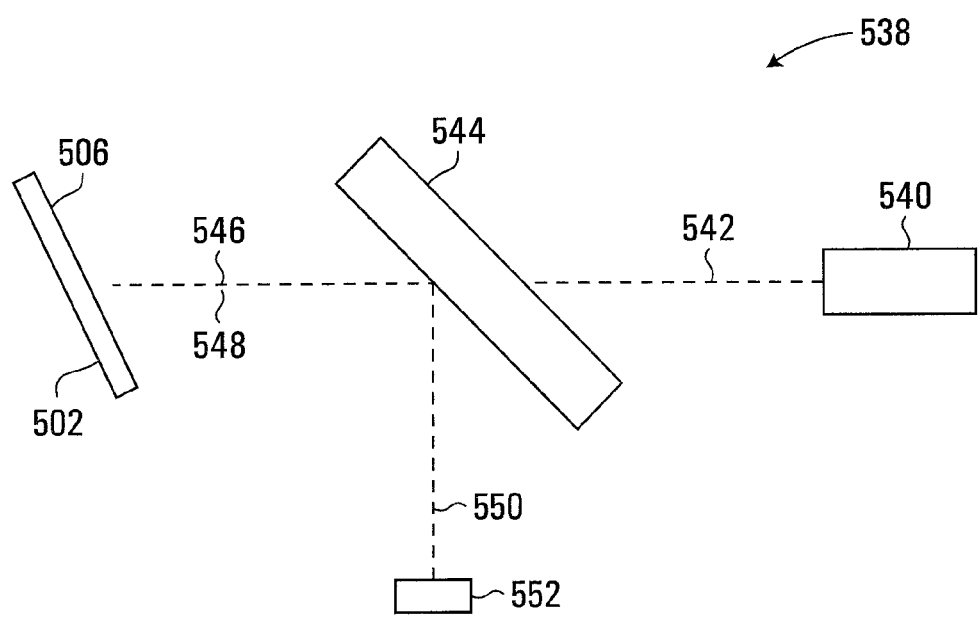
FIG. 36 is a schematic illustration of an illustrative detection apparatus.

Referring to FIG. 36, an illustrative detection apparatus is shown generally at 538 and includes a light source 540 directing a light beam 542 to a beam splitter 544. A portion of the light beam 542 passes through the beam splitter 544 in a light beam 546 towards a portion of the capture surface 506 of the assembly 502 (illustrated in FIG. 33). The light beam 546 is reflected from that portion of the capture surface 506 in a reflected light beam 548 that is generally parallel to the light beam 546 and in an intensity proportional to the concentration of pathogens on that portion of the capture surface 506. The reflected light beam 548 is received at the beam splitter 544, and a portion of the reflected light beam 548 is reflected in a reflected light beam 550 to an optical sensor, which in the embodiment shown is a digital camera 552.

Alternative embodiments may include other types of optical sensor. Accordingly, the intensity of light received at the digital camera may be proportional to the concentration of pathogens on the portion of the capture surface 506 reflecting light from the beam splitter 544. Capture surfaces, such as those discussed above, may be moved relative to the light beam 546 so that over a time series of measurements, the digital camera 552 may record intensities of light indicating a number of pathogens on the capture surfaces.

By measuring a number of pathogens on the capture surfaces as described above, a concentration of pathogens may be determined in relatively less time than when compared to filtration or other methods for detecting such pathogens. For example, the process described above may require less than an hour to determine whether a particular substance or substances are carried in a sample of a fluid such as water.

While specific embodiments have been described and illustrated, such embodiments should be considered illustrative only and not as limiting the invention as construed in accordance with the accompanying claims.

What is claimed is:

1. An apparatus for determining whether a substance is carried in a fluid, the apparatus comprising:
   a fluid conduit defining a fluid inlet and a fluid outlet, the fluid conduit configured to direct flow of the fluid through the fluid conduit between the fluid inlet and the fluid outlet; and
   at least one removable element having at least one capture surface removably positioned in the fluid conduit and configured to contact the fluid as the fluid flows through the fluid conduit between the fluid inlet and the fluid outlet, the at least one capture surface coated with a plurality of capture molecules, having respective binding affinities with the substance, to capture the substance from the fluid;
   wherein the apparatus defines at least one fluid guiding surface in the fluid conduit, the at least one fluid guiding surface opposite, and spaced apart by a predetermined distance from, a respective one of the at least one capture surface to guide flow of the fluid and the substance over the plurality of capture molecules on the respective one of the at least one capture surface in a gap between the at least one fluid guiding surface and the respective one of the at least one capture surface as the fluid flows through the fluid conduit between the fluid inlet and the fluid outlet.

2. The apparatus of claim 1 wherein the at least one capture surface comprises a plurality of capture surfaces, and wherein the at least one fluid guiding surface comprises a plurality of fluid guiding surfaces spaced apart by respective predetermined distances from respective ones of the plurality of capture surfaces to guide the flow of the fluid and the substance over the plurality of capture molecules on the plurality of capture surfaces in gaps between respective ones of the plurality of fluid guiding surfaces and the respective ones of the plurality of capture surfaces as the fluid flows through the fluid conduit between the fluid inlet and the fluid outlet.

3. The apparatus of claim 2 wherein the at least one element comprises a plurality of cylindrical elements each having a curved cylindrical outer surface having at least one of the plurality of capture surfaces.

4. The apparatus of claim 3 wherein the plurality of fluid guiding surfaces comprises, for each one of the plurality of capture surfaces, at least a portion of the curved cylindrical outer surface of an adjacent one of the plurality of cylindrical elements.

5. The apparatus of claim 3 wherein the cylindrical elements extend generally parallel to each other.

6. The apparatus of claim 2 wherein the plurality of capture surfaces and the plurality of fluid guiding surfaces are configured to generate electric fields between each one of the plurality of capture surfaces and each respective one of the plurality of fluid guiding surfaces to urge the substance in the fluid towards the plurality of capture surfaces.

7. The apparatus of claim 6 wherein each one of the plurality of spaced-apart capture surfaces is electrically grounded, and wherein each one of the plurality of fluid guiding surfaces is electrically connected to a voltage source.

8. The apparatus of claim 2 wherein the at least one element comprises a plurality of longitudinally spaced-apart plates each having at least one of the plurality of capture surfaces.

9. The apparatus of claim 8 wherein each one of the plurality of plates has at least one wall and defines at least one longitudinal fluid through-opening longitudinally aligned with the at least one wall of each adjacent one of the plurality of plates.

10. The apparatus of claim 9 wherein the plurality of fluid guiding surfaces comprises, for each one of the plurality of capture surfaces, at least a portion of a surface of the at least one wall of an adjacent one of the plurality of plates.

11. The apparatus of claim 9 further comprising at least one spacer separating adjacent ones of the plurality of plates.

12. The apparatus of claim 11 wherein the at least one spacer surrounds a respective region that is between adjacent ones of the plurality of plates and that is in fluid communication with the at least one fluid through-opening of the adjacent ones of the plurality of plates.

13. The apparatus of claim 12 wherein each spacer has a thickness equal to the respective predetermined distance of at least one of the plurality of fluid guiding surfaces and of at least one of the plurality of capture surfaces in the respective region of each spacer.

14. The apparatus of claim 12 wherein the at least one spacer seals the respective region.

15. The apparatus of claim 8 wherein the plates extend generally parallel to each other.

16. The apparatus of claim 15 wherein the plurality of fluid guiding surfaces are configured to guide the flow of the fluid and the substance over the plurality of capture molecules on the respective ones of the plurality of capture surfaces in a direction generally parallel to the plates.

17. The apparatus of claim 8 further comprising a plurality of longitudinally spaced walls longitudinally spaced from opposite sides of each one of the plurality of plates and defining a respective region surrounding each one of the plurality of plates, wherein:
   the apparatus defines at least one opening for communicating fluid between adjacent ones of the regions; and
   the plurality of fluid guiding surfaces comprises, for each one of the plurality of capture surfaces, at least a portion of a surface of an adjacent one of the plurality of walls.

18. The apparatus of claim 17 wherein:
   each one of the plurality of plates has first and second opposite and generally circular sides each having a center and a peripheral region;
   the at least one opening is configured to communicate fluid between the centers of adjacent sides of adjacent ones of the plurality of plates; and
   for each one of the plurality of plates, the respective region surrounding the plate is configured to direct fluid received at the center of the first side of the plate to the peripheral region of the first side of the plate, then to the peripheral region of the second side of the plate, and then to the center of the second side of the plate.

19. The apparatus of claim 1 wherein the at least one capture surface is oriented in the apparatus to be contacted by the fluid in an incidental flow.

\* \* \* \* \*